(12) United States Patent  (10) Patent No.: US 8,354,431 B2
Hersperger et al.  (45) Date of Patent: Jan. 15, 2013

(54) ARYL CARBOXYLIC ACID CYCLOHEXYL AMIDE DERIVATIVES

(75) Inventors: Rene Hersperger, Munchenstein (CH); Philipp Janser, Basel (CH); Wolfgang Miltz, Basel (CH)

(73) Assignee: Novartis AG, Basel (CH)

( * ) Notice: Subject to any disclaimer, the term of this patent is extended or adjusted under 35 U.S.C. 154(b) by 382 days.

(21) Appl. No.: 12/527,469

(22) PCT Filed: Feb. 18, 2008

(86) PCT No.: PCT/EP2008/051951
§ 371 (c)(1), (2), (4) Date: Aug. 17, 2009

(87) PCT Pub. No.: WO2008/101905
PCT Pub. Date: Aug. 28, 2008

(65) Prior Publication Data
US 2010/0016361 A1    Jan. 21, 2010

(30) Foreign Application Priority Data

Feb. 19, 2007   (EP) ..................................... 07102622

(51) Int. Cl.
A61K 31/445   (2006.01)
C07D 401/14   (2006.01)

(52) U.S. Cl. ....................... 514/323; 546/201
(58) Field of Classification Search .................. 514/323; 546/201
See application file for complete search history.

(56) References Cited

U.S. PATENT DOCUMENTS

| | | | |
|---|---|---|---|
| 6,235,771 B1 | 5/2001 | Shiraishi et al. | |
| 6,312,689 B1 | 11/2001 | LaRosa | |
| 7,858,781 B2 * | 12/2010 | Hersperger et al. | 540/602 |
| 2006/0251651 A1 | 11/2006 | Shibayama et al. | |
| 2007/0270429 A1 | 11/2007 | Shibayama et al. | |
| 2008/0076120 A1 | 3/2008 | Donaldson et al. | |
| 2008/0107647 A1 | 5/2008 | Ma et al. | |
| 2008/0241167 A1 | 10/2008 | Combadiere et al. | |

FOREIGN PATENT DOCUMENTS

| | | |
|---|---|---|
| EP | 0 834 564 A2 | 4/1998 |
| WO | 95/19436 A1 | 7/1995 |
| WO | 97/32019 A2 | 9/1997 |
| WO | 98/32438 A1 | 7/1998 |
| WO | 99/32100 | 7/1999 |
| WO | 99/32100 A | 7/1999 |
| WO | 01/51077 A1 | 7/2001 |
| WO | 02/20615 A2 | 3/2002 |
| WO | 03/030897 A1 | 4/2003 |
| WO | 2005/060665 A2 | 7/2005 |
| WO | 2005/077932 A | 8/2005 |
| WO | 2005/115392 A2 | 12/2005 |
| WO | 2005/118579 A2 | 12/2005 |
| WO | 2007/027734 A2 | 3/2007 |
| WO | 2007/062175 A2 | 5/2007 |
| WO | 2007/071952 A1 | 6/2007 |
| WO | 2007/144720 A2 | 12/2007 |
| WO | 2008/045564 A2 | 4/2008 |
| WO | 2008/060621 A2 | 5/2008 |
| WO | 2008/060783 A2 | 5/2008 |
| WO | 2008/099278 A2 | 8/2008 |
| WO | 2008/134076 A1 | 11/2008 |

OTHER PUBLICATIONS

Fed. Regter "examination guidelines update . . . " p. 1-34 (2010).*

* cited by examiner

Primary Examiner — Celia Chang
(74) Attorney, Agent, or Firm — Sophie Binet Cross

(57) ABSTRACT

A compound of formula (I) or a pharmaceutically acceptable salt or prodrug ester thereof: (I) wherein the variants R and X are defined in the specification.

(I)

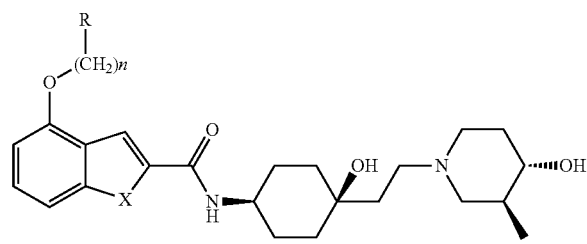

7 Claims, No Drawings

ARYL CARBOXYLIC ACID CYCLOHEXYL AMIDE DERIVATIVES

This application is a U.S. national Phase filing of international Serial No. PCT/EP2008/051951 filed Feb. 18, 2008, and claims priority to EP application Serial No. 07102622.3 filed Feb. 19, 2007, the contents of which are incorporated herein by reference in their entirety.

The invention relates to bicyclic carbonyl amino derivatives which are antagonists of Chemokine Receptor 2 (CCR-2) and Chemokine Receptor 5 (CCR-5), and to their use in the treatment of diseases and disorders which involve migration and activation of monocytes and T-cells, including inflammatory diseases.

Accordingly the invention in a first aspect provides a compound of formula (I), or a pharmaceutically acceptable salt or prodrug ester thereof:

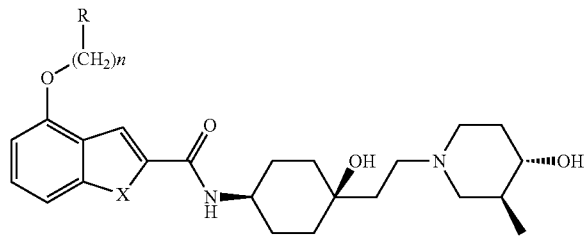

(I)

Wherein:
X is $CH_2$ or NH;
n is 1 or 2;
R is selected from C3-C18 cycloalkyl, C3-C18 heterocycloalkyl, C3-C18 heteroaryl, C3-C18 aryl;
R optionally has fused to it a group B selected from C3-C8 cycloalkyl, C3-C8 heterocycloalkyl, C3-C8 aryl and C3-C8 heteroaryl;
and R and B are each independently unsubstituted or substituted by R1 which defines one or more groups independently selected from halo, C1-C7 alkoxy, oxo, C1-C7 alkyl, C1-C7 alkoxy-C1-C7 alkoxy, C2-C7 alkenyl, C2-C7 alkenyloxy, amino, aminocarbonyl, carbamoyl, mono- or di-C1-C7 alkylamino, hydroxyl, cyano, mercapto, $C_1$-$C_7$ alkoxycarbonyl, aryl, heteroaryl, carboxy, sulfanyl, sulfonyl; R1 being itself unsubstituted or substituted by one or more groups selected from halo, hydroxyl, cyano, C1-C6 alkyl, C1-C6 alkoxy, C2-C7 alkenyl, C2-C7 alkenyloxy, amino, aminocarbonyl, carbamoyl, mono- or di-C1-C7 alkylamino, hydroxyl, cyano, mercapto, $C_1$-$C_7$ alkoxycarbonyl, aryl, heteroaryl, carboxy.

For the avoidance of doubt, the terms listed below are to be understood to have the following meaning throughout the present description and claims:

The term "lower", when referring to organic radicals or compounds means a compound or radical with may be branched or unbranched with up to and including 7 carbon atoms.

A lower alkyl group may be branched, unbranched or cyclic and contains 1 to 7 carbon atoms, preferably 1 to 4 carbon atoms. Lower alkyl represents, for example: methyl, ethyl, propyl, butyl, isopropyl, isobutyl, tertiary butyl or 2,2-dimethylpropyl.

A lower alkoxy group may be branched or unbranched and contains 1 to 7 carbon atoms, preferably 1 to 6 carbon atoms. Lower alkoxy represents, for example: methoxy, ethoxy, propoxy, butoxy, isopropoxy, isobutoxy or tertiary butoxy. Lower alkoxy includes cycloalkyloxy and cycloalkyl-lower alkyloxy.

A lower alkene, alkenyl or alkenoxy group is branched or unbranched and contains 2 to 7-carbon atoms, preferably 1 to 4 carbon atoms and contains at least one carbon-carbon double bond. Lower alkene, lower alkenyl or lower alkenyloxy represents for example vinyl, prop-1-enyl, allyl, butenyl, isopropenyl or isobutenyl and the oxy equivalents thereof.

In the present application, oxygen containing substituents, e.g. alkoxy, alkenyloxy, alkynyloxy, carbonyl, etc. encompass their sulphur containing homologues, e.g. thioalkoxy, thioalkenyloxy, thioalkynyloxy, thiocarbonyl, sulphone, sulphoxide etc.

Halo or halogen represents chloro, fluoro, bromo or iodo.
Aryl represents carbocyclic aryl, heteroaryl or biaryl.

Carbocyclic aryl is an aromatic cyclic hydrocarbon containing from 6 to 18 ring atoms. It can be monocyclic, bicyclic or tricyclic, for example naphthyl, phenyl, or phenyl mono-, di- or trisubstituted by one, two or three substituents.

Heteroaryl is an aromatic monocyclic or bicyclic hydrocarbon containing from 5 to 18 ring atoms one or more of which are heteroatoms selected from O, N or S. Heteroaryl can be mono-, bi-, or tricyclic. Preferably there are one or two heteroatoms. Heteroaryl represents, for example: pyridyl, indolyl, quinoxalinyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl, thienyl, thiazolyl. Heteroaryl also includes such substituted radicals.

Cycloalkyl represents a mono-, di- or tricyclic hydrocarbon which may be saturated or unsaturated containing from 3 to 18 ring atoms, preferably from 3 to 6 ring atoms. Cycloalkyl includes bridged and fused ring systems. Cycloalkyl represents, for example: cyclopropyl, cyclobutyl, cyclopentyl, or cyclohexyl. The cycloalkyl may optionally be substituted.

Heterocycloalkyl represents a mono-, di- or tricyclic hydrocarbon which may be saturated or unsaturated and which contains one or more, preferably one to three heteroatoms selected from O, N or S. Preferably it contains between three and 18 ring atoms. The term heterocycloalkyl is intended also to include fused and bridged heterocycloalkyl groups such as 3-hydroxy-8-aza-bicyclo[3.2.1]oct-8-yl.

Pharmaceutically acceptable prodrug esters are ester derivatives which are convertible by solvolysis or under physiological conditions to the free carboxylic acid of formula (I). Such esters are for example lower alkyl esters (such as methyl or ethyl esters), carboxy-lower alkyl esters such as the carboxymethyl ester, nitrooxy-lower alkyl esters (such as the 4-nitrooxybutyl ester).

Referring to formula (I), preferably X is NH.
Preferably n is 1.
R is preferably selected from unsubstituted or substituted C3-C18 heteroaryl optionally having fused to it a group B selected from C3-C8 cycloalkyl, C3-C8 heterocycloalkyl, C3-C8 aryl and C3-C8 heteroaryl;

R and B are each independently unsubstituted or substituted by R1 as defined above.

R is more preferably thiazoyl, pyridinyl, benzofuranyl, benzofuranyl or 4,5,6,7-tetrahydro-benzofuranyl which is unsubstituted or substituted by R1 as defined above.

R is yet more preferably benzofuranyl which is unsubstituted or substituted by R1 as defined above.

Alternatively preferably, R is C3-C18 heterocycloalkyl optionally having fused to it a group B selected from C3-C8 cycloalkyl, C3-C8 heterocycloalkyl, C3-C8 aryl and C3-C8 heteroaryl;

R and B are each independently unsubstituted or substituted by R1 as defined above.

Yet more preferably, R is or tetrahydrofuranyl or 2,3-dihydrobenzofuranyl. In each case, R is unsubstituted or substituted as defined above.

Preferred compounds of formula I are:

4-Cyclobutylmethoxy-1H-indole-2-carboxylic acid {4-hydroxy-4-[2-((3S,4S)-4-hydroxy-3-methyl-piperidin-1-yl)-ethyl]-cyclohexyl}-amide 4-(Tetrahydro-furan-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide 4-(Furan-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide 4-(2-Chloro-thiazol-4-ylmethoxy)-1H-indole-2-carboxylic acid {4-hydroxy-4-[2-((3S,4S)-4-hydroxy-3-methyl-piperidin-1-yl)-ethyl]-cyclohexyl}-amide 4-(6-Methoxy-pyridin-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide 4-(4-Oxo-4,5,6,7-tetrahydro-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide 4-(6,6-Dimethyl-4-oxo-4,5,6,7-tetrahydro-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide 4-[(S)-1-(2,3-Dihydro-benzofuran-3-yl)methoxy]-1H-indole-2-carboxylic acid {4-hydroxy-4-[2-((3S,4S)-4-hydroxy-3-methyl-piperidin-1-yl)-ethyl]-cyclohexyl}-amide 4-((R,S)-6-Methoxy-2,3-dihydro-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide 4-(4-Methoxy-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide 4-(4,6-Difluoro-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide 4-(5-Chloro-benzofuran-3-ylmethoxy)-1H-indole-2-carboxylic acid {4-hydroxy-4-[2-((3S,4S) 4-hydroxy-3-methyl-piperidin-1-yl)-ethyl]-cyclohexyl}-amide 4-(6-Methoxy-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide 4-(6-Ethoxy-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide 4-(6-Cyclopropylmethoxy-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide 4-[6-(2-Ethoxy-ethoxy)-benzofuran-3-ylmethoxy]-1H-indole-2-carboxylic acid {4-hydroxy-4-[2-((3S,4S)-4-hydroxy-3-methyl-piperidin-1-yl)-ethyl]-cyclohexyl}-amide 4-[6-((RS)-2-Methoxy-1-methyl-ethoxy)-benzofuran-3-ylmethoxy]-1H-indole-2-carboxylic acid {4-hydroxy-4-[2-((3S,4S)-4-hydroxy-3-methyl-piperidin-1-yl)-ethyl]-cyclohexyl}-amide 4-[6-(2-Isopropoxy-ethoxy)-benzofuran-3-ylmethoxy]-1H-indole-2-carboxylic acid {4-hydroxy-4-[2-((3S,4S)-4-hydroxy-3-methyl-piperidin-1-yl)-ethyl]-cyclohexyl}-amide 4-[6-(3-Methoxy-propoxy)-benzofuran-3-ylmethoxy]-1H-indole-2-carboxylic acid {4-hydroxy-4-[2-((3S,4S)-4-hydroxy-3-methyl-piperidin-1-yl)-ethyl]-cyclohexyl}-amide 4-[6-(3-Ethoxy-propoxy)-benzofuran-3-ylmethoxy]-1H-indole-2-carboxylic acid {4-hydroxy-4-[2-((3S,4S)-4-hydroxy-3-methyl-piperidin-1-yl)-ethyl]-cyclohexyl}-amide 4-{6-[(S)-(Tetrahydro-furan-3-yl)oxy]-benzofuran-3-ylmethoxy}-1H-indole-2-carboxylic acid {4-hydroxy-4-[2-((3S,4S)-4-hydroxy-3-methyl-piperidin-1-yl)-ethyl]-cyclohexyl}-amideamide 4-(6-Fluoro-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide 4-(7-Methoxy-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide 4-[2-(2-Methoxy-phenyl)-ethoxy]-1H-indole-2-carboxylic acid {4-hydroxy-4-[2-((3S,4S)-4-hydroxy-3-methyl-piperidin-1-yl)-ethyl]-cyclohexyl}-amide 4-[2-(3-Methoxy-phenyl)-ethoxy]-1H-indole-2-carboxylic acid {4-hydroxy-4-[2-((3S,4S)-4-hydroxy-3-methyl-piperidin-1-yl)-ethyl]-cyclohexyl}-amide 4-[2-(4-Methoxy-phenyl)-ethoxy]-1H-indole-2-carboxylic acid {4-hydroxy-4-[2-((3S,4S)-4-hydroxy-3-methyl-piperidin-1-yl)-ethyl]-cyclohexyl}-amide 4-[2-(2-Methoxy-pyridin-3-yl)-ethoxy]-1H-indole-2-carboxylic acid {4-hydroxy-4-[2-((3S,4S)-4-hydroxy-3-methyl-piperidin-1-yl)-ethyl]-cyclohexyl}-amide 4-[2-(6-Methoxy-pyridin-3-yl)-ethoxy]-1H-indole-2-carboxylic acid {4-hydroxy-4-[2-((3S,4S)-4-hydroxy-3-methyl-piperidin-1-yl)-ethyl]-cyclohexyl}-amide 4-[2-(6-Methoxy-benzofuran-3-yl)-ethoxy]-1H-indole-2-carboxylic acid {4-hydroxy-4-[2-((3S,4S)-4-hydroxy-3-methyl-piperidin-1-yl)-ethyl]-cyclohexyl}-amide According to a second aspect of the invention there is provided a compound of formula (I) for use as a pharmaceutical for the prevention, amelioration or treatment of an autoimmune or inflammatory disease or condition.

According to a third aspect of the invention there is provided a process for the preparation of a compound of formula (I) comprising reacting a compound of formula (III):

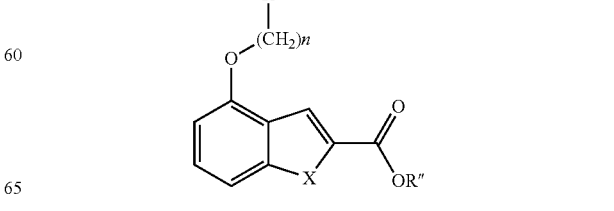

wherein R" is H or a $C_1$-$C_7$ alkyl group, with a compound of formula (IV)

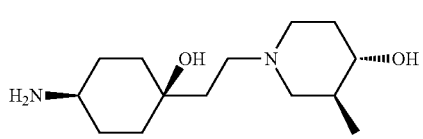
(IV)

and recovering the resultant compound of formula (I) in free or salt form.

The process of the invention is effected in conventional manner.

The process is a condensation reaction between acid or ester and amine. It is conveniently effected by reacting the acid with the amine in the presence of coupling agents, for example TBTU/DIEA in a solvent such as DMF, or by reacting the ester with the amine in the presence of a coupling agent such as HOBT/EDC.

The appropriate compound of formula (III) may be prepared as described below according to the reaction scheme 4, from 4-hydroxy-1H-indole-2-carboxylic ethyl ester, which can itself be prepared as outlined in scheme 1.

The compound of formula (IV) may be prepared according to schemes 2 and 3 below.

The compounds of the invention can be recovered from the reaction mixture and purified in conventional manner. Isomers, such as enantiomers, may be obtained in conventional manner, e.g. by fractional crystallization or asymmetric synthesis from corresponding asymmetrically substituted, e.g. optically active, starting materials.

The starting materials and intermediates are either known or can be prepared according to known methods or analogously as described in the Examples.

According to a fourth aspect of the invention there is provided compound obtainable by any one of the above mentioned processes.

According to a fifth aspect of the invention there is provided a pharmaceutical composition comprising a compound of formula (I) in association with a pharmaceutically acceptable diluent or carrier.

According to a sixth aspect of the invention there is provided the use of a compound of formula (I) in the manufacture of a medicament for use in the treatment of an autoimmune or inflammatory disease or condition.

According to a seventh aspect of the invention there is provided a method of inhibiting chemokine receptors or macrophage proteins or of reducing inflammation in a subject in need of such treatment, which method comprises administering to said subject an effective amount of a compound of formula (I).

According to an eighth aspect of the invention there is provided a method of treating an inflammatory or autoimmune disease or condition, comprising administering to said subject an effective amount of a compound of formula (I).

Agents of the invention may be prepared by processes described below:

EXPERIMENTAL SECTION

Abbreviations

BOC: t-Butyloxycarbonyl
Boc2O: Di-t-butyl dicarbonate
BuLi: n-Butyl lithium
DCM: Dichloromethane
DEAD: Diethyl azadicarboxylate
DIEA: Ethyl-diisopropyl-amine
DMAP: Dimethyl-pyridin-4-yl-amine
DMF: N,N-Dimethyl formamide
DMSO: Dimethylsulfoxide
EDC: (3-Dimethylamino-propyl)-ethyl-carbodiimide hydrochloride
Ether: Ethoxy-ethane
EtOH: Ethanol
EtOAc: Acetic acid ethyl ester
HCl: Hydrochloric acid
HOBT: Benzotriazol-1-ol
LAH: Lithium aluminumhydride
MeOH: Methanol
NaOH: Sodium hydroxide
NMP: 1-Methyl-pyrrolidin-2-one
Pd/C: Palladium on carbon
RT: room temperature
TBTU O-(1H-benzotriazol-1-yl)-N,N,N',N'-tetramethyluronium tetrafluoroborate
t-BuOH 2-Methyl-propan-2-ol
THF: Tetrahydrofuran
TLC: Thin layer chromatography 1H-NMR spectra are recorded on a Varian Gemini 400 MHz NMR spectrometer. Significant peaks are tabulated in the order: multiplicity (s, singlet; d, doublet; t, triplet; q, quartet; m, multiplet; br, broad) and number of protons. Electron Spray Ionization (ESI) mass spectra are recorded on a Hewlett Packard 5989A mass spectrometer. Mass spectrometry results are reported as the ratio of mass over charge. Preparative HPLC purifications are performed with XTerra™ RP18 19×150 mm columns, using acetonitrile/water or MeOH/water as eluent systems. All reagents, starting materials and intermediates utilized in these examples are available from commercial sources or are readily prepared by methods known to those skilled in the art.

Synthesis of the Indol Building Block

The indol building block 2 is prepared according the reaction scheme outlined below.

Reaction Scheme 1:

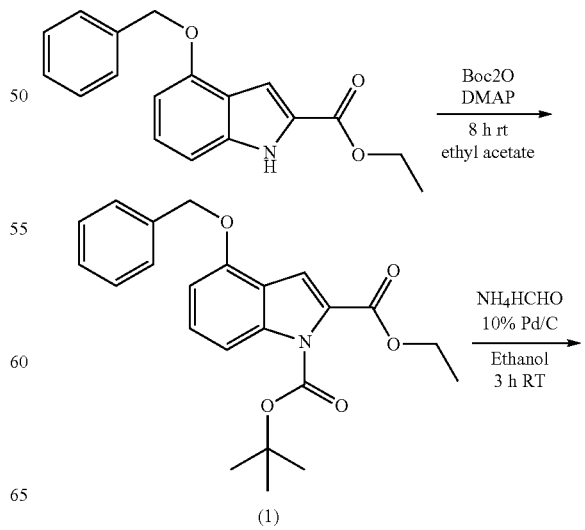
(1)

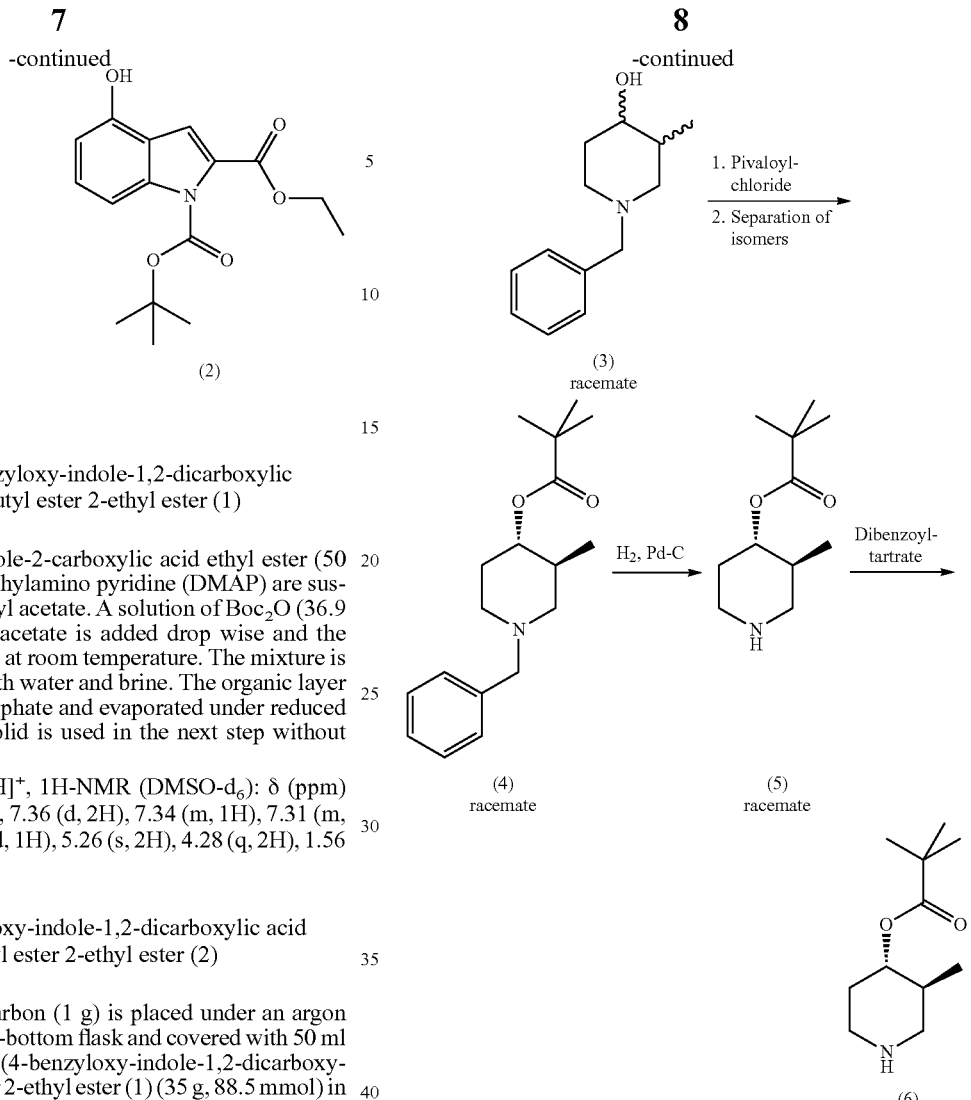

(2)

(1) Step A: 4-Benzyloxy-indole-1,2-dicarboxylic acid 1-tert-butyl ester 2-ethyl ester (1)

4-Benzyloxy-1H-indole-2-carboxylic acid ethyl ester (50 g, 169 mmol) and dimethylamino pyridine (DMAP) are suspended in 100 ml of ethyl acetate. A solution of Boc$_2$O (36.9 g, 169 mmol) in ethyl acetate is added drop wise and the mixture is stirred for 5 h at room temperature. The mixture is washed successively with water and brine. The organic layer is dried over sodium sulphate and evaporated under reduced pressure. The yellow solid is used in the next step without further purification.

MS (ESI): 396 [M+H]$^+$, 1H-NMR (DMSO-d$_6$): δ (ppm) 7.5 (d, 1H), 7.48 (d, 2H), 7.36 (d, 2H), 7.34 (m, 1H), 7.31 (m, 1H), 7.22 (s, 1H), 6.92 (d, 1H), 5.26 (s, 2H), 4.28 (q, 2H), 1.56 (s, 9H), 1.31 (t, 3H).

(2) Step B: 4-Hydroxy-indole-1,2-dicarboxylic acid 1-tert-butyl ester 2-ethyl ester (2)

10% Palladium on carbon (1 g) is placed under an argon atmosphere into a round-bottom flask and covered with 50 ml of ethanol. A solution of (4-benzyloxy-indole-1,2-dicarboxylic acid 1-tert-butyl ester 2-ethyl ester (1) (35 g, 88.5 mmol) in 250 ml ethanol is added, followed by ammonium formiate (6.3 g, 97.4 mmol). The mixture is stirred for 30 min at rt (TLC control). After completion of the reaction, the mixture is filtrated and evaporation gives a white solid, which is further purified by recrystallization from diethyl ether/hexanes.

MS (ESI): 208 [M]$^+$, 1H-NMR (DMSO-d$_6$): δ (ppm) 10.2 (br, 1H), 7.4 (d, 1H), 7.28 (s, 1H), 7.25 (dd, 1H), 6.67 (d, 1H), 4.3 (q, 2H), 1.53 (s, 9H), 1.3 (t, 3H).

Synthesis of the Amine Building Blocks

The amine building blocks 6 and 14 are prepared according the reaction scheme outlined below.

Reaction Scheme 2:

Synthesis of 2,2-Dimethyl-propionic acid (3S,4S)-3-methyl-piperidin-4-yl ester (6)

(1) Step A: (1-RS,3-RS)-1-Benzyl-3-methyl-piperidin-4-ol (3)

1-Benzyl-3-methyl-4-piperidone (25 g, 123 mmol) is dissolved in 200 ml of methanol and stirred at rt. NaBH$_4$ (2.3 g, 61.5 mmol) is added in small portions during 1 h (exothermic reaction, 30° C.). The yellow solution is stirred for additional 30 min at room temperature. Then the mixture is evaporated under reduced pressure, dissolved in ethyl acetate and washed with water.

MS (ESI): 205 [M]$^+$, 1H-NMR (CDCl$_3$): δ (ppm) 7.15-7.3 (m, 5H), 4.5 and 4.3 (d, OH), 3.38 (s, 2H), 3.55 and 2.89 (m, 1H), 2.6-2.75 (m, 2H), 1.9 (dt, 1H), 1.7 (m, 1H), 1.65 (m, 1H), 1.3-1.5 (m, 2H), 0.84 (d, 3H).

(2) Step B: 2,2-Dimethyl-propionic acid (3RS,4RS)-1-benzyl-3-methyl-piperidin-4-yl ester (4)

(1-RS,3-RS)-1-Benzyl-3-methyl-piperidin-4-ol (3) (24.9 g, 121 mmol) is dissolved in 500 ml of dry THF. Triethylamine (25.4 ml, 182 mmol) is added, followed by slow addition of pivaloylchloride (21.9 g, 182 mmol). The reaction mixture is heated under reflux over night (80° C.). The mixture is filtered off and diluted with diethyl ether. The organic layer is washed with 1N aqueous sodium hydroxide solution and brine, dried over Na$_2$SO$_4$ and evaporated under reduced pressure. The crude product (cis/trans mixture) is purified by flash chromatography (silica gel, ethyl acetate/hexanes 5:95) to obtain the pure trans isomer.

MS (ESI): 290 [M+H]$^+$, 1H-NMR (CDCl$_3$): δ (ppm) 7.28 (m, 5H), 4.75 (m, 1H), 3.42 (d, 2H), 2.5 (m, 2H), 1.9-2.2 (m, 3H), 1.7 (m, 2H), 1.15 (s, 9H), 0.78 (d, 3H).

(3) Step C: 2,2-Dimethyl-propionic acid (3RS,4RS)-3-methyl-piperidin-4-yl ester (5)

Palladium hydroxide (20% on carbon, 1.5 g) is placed in a round-bottom flask under an argon atmosphere and covered with methanol, A solution of 2,2-dimethyl-propionic acid (3RS,4RS)-1-benzyl-3-methyl-piperidin-4-yl ester (4) (15 g, 51.8 mmol) in 300 ml of methanol is added, followed by an 1.3M methanolic HCl solution (62 ml, 78 mmol). Then the mixture is hydrogenated under normal pressure for 20 h. The solution is filtrated through celite and evaporated under reduced pressure. The residue is dissolved in diethyl ether and washed with 1N aqueous sodium hydroxide solution and brine. The combined organic layers are dried over Na$_2$SO$_4$ and evaporated under reduced pressure.

MS (ESI): 200 [M+H]$^+$, 1H-NMR (CDCl$_3$): δ (ppm) 4.32 (dt, 1H), 3.3 (br, 1H), 2.85 (m, 2H), 2.45 (dt, 1H), 2.15 (dd, 1H), 1.75 (m, 1H), 1.55 (m, 1H), 1.27 (m, 1H), 1.13 (s, 9H), 0.78 (d, 3H).

(4) Step D: 2,2-Dimethyl-propionic acid (3S,4S)-3-methyl-piperidin-4-yl ester (−)-dibenzoyltartrate (6)

2,2-Dimethyl-propionic acid (3RS,4RS)-3-methyl-piperidin-4-yl ester (5) (9.6 g, 48 mmol) is dissolved in 50 ml of ethyl acetate. A solution of (−)-dibenzoyltartrate (8.6 g, 24 mmol) in ethyl acetate is added drop wise. The precipitate is filtrated off and washed with cold ethyl acetate to yield colourless crystals.

Reaction Scheme 3:

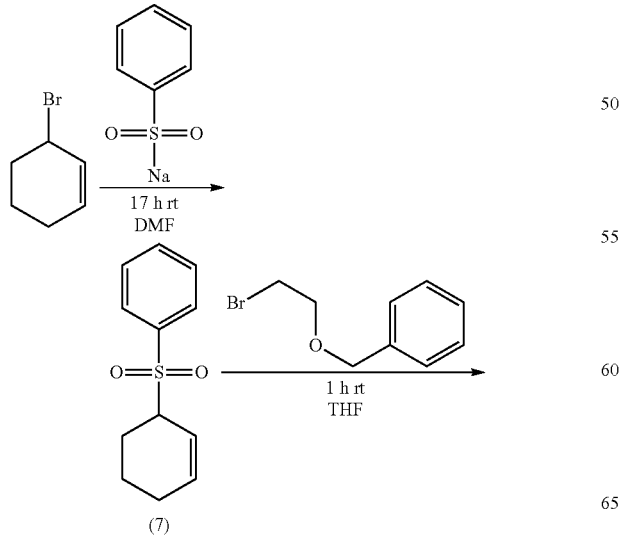

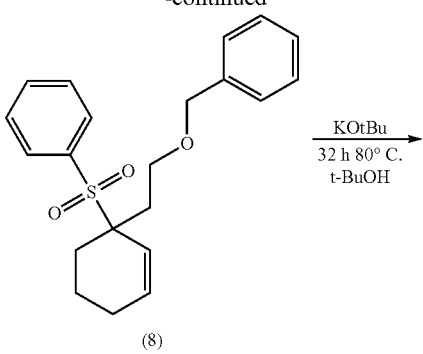

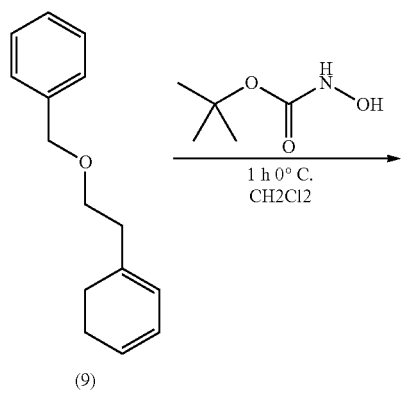

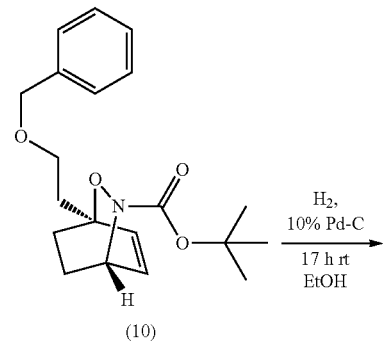

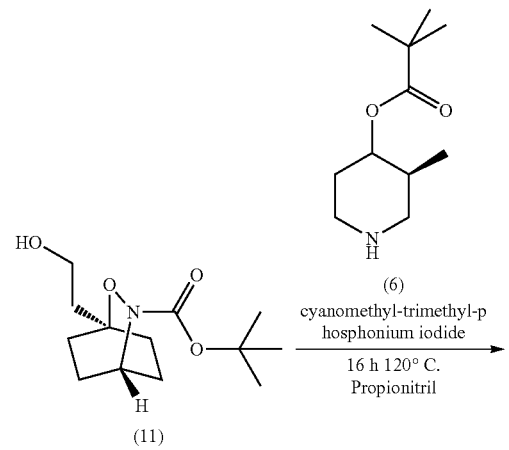

MS (ESI): 357.2 [M+H]⁺, 1H-NMR (CDCl₃): δ (ppm) 7.85 (d, 2H), 7.85 (dd, 1H), 7.55 (dd, 2H), 7.25-7.35 (m, 5H), 6.15 (m, 1H), 5.65 (d, 1H), 4.45 (s, 2H), 3.5-3.8 (m, 3H), 1.4-2.3 (m, 7H).

(3) Step C: (2-Cyclohexa-1,3-dienyl-ethoxymethyl)-benzene (9)

[2-(1-Benzenesulfonyl-cyclohex-2-enyl)-ethoxymethyl]-benzene (8) (16 g, 44.9 mmol) is dissolved in tert. butanol (450 ml) and after addition of potassium tert.-butoxide (11.1 g, 98.7 mmol) the mixture is stirred for 32 h at 80° C. Then the mixture is poured on ice and extracted with pentane. The organic layer is separated, washed with saturated NaCl-solution and dried over $Na_2SO_4$. The crude product is purified by Flash-chromatography (ethyl acetate/hexanes (1:9), silicagel).

MS (ESI): 215 [M+H]⁺, 1H-NMR (CDCl₃): δ (ppm) 7.2-7.4 (m, 5H), 5.84 (m, 1H), 5.65 (m, 2H), 4.45 (m, 2H), 3.55 (t, 2H), 2.32 (t, 2H), 2.0-2.3 (m, 4H).

(4) Step D: (1S,4S)-1-(2-Benzyloxy-ethyl)-2-oxa-3-aza-bicyclo[2.2.2]oct-5-ene-3-carboxylic acid tert-butyl ester (10)

(2-Cyclohexa-1,3-dienyl-ethoxymethyl)-benzene (9) (6 g, 28 mmol) is dissolved in 280 ml of dry methylene chloride and cooled down to 0° C. After addition of molecular sieves (6 g, UOP Type 4A) and N—BOC-hydroxylamine (5.6 g, 42 mmol) in small portions, tetrapropylammonium(meta)periodate (10.8 g, 28 mmol) is added slowly in small portions the mixture was stirred for 1 h. Then the mixture is diluted with $CH_2Cl_2$ and cooled to −10° C. 2M $Na_2S_2O_5$ solution is added slowly (exothermic!). The mixture is washed with water, dried over $Na_2SO_4$ and evaporated under reduced pressure. The crude product is purified by Flash-chromatography (ethyl acetate/hexanes (1:9), silicagel).

MS (ESI): 346 [M+H]⁺, 1H-NMR (CDCl₃): δ (ppm) 7.3 (m, 5H), 6.53 (dd, 1H), 6.44 (dd, 1H), 4.56 (m, 1H), 4.45 (s, 2H), 3.62 (m, 1H), 1.5-2.1 (m, 6H), 1.34 (s, 9H).

(5) Step E: 1-(2-Hydroxy-ethyl)-2-oxa-3-aza-bicyclo[2.2.2]octane-3-carboxylic acid tert-butyl ester (11)

1 g Pd—C is placed into an round-bottom flask under an argon atmosphere and covered with ethanol. A solution of (1S,4S)-1-(2-benzyloxy-ethyl)-2-oxa-3-aza-bicyclo[2.2.2]oct-5-ene-3-carboxylic acid tert-butyl ester (10) (2 g, 5.8 mmol) in 58 ml of ethanol is added and the mixture is hydrogenated at rt for 6 h. Then the mixture is filtrated over celite and evaporated under reduced pressure. The product was used in the next step without further purification.

MS (ESI): 258 [M+H]⁺, 1H-NMR (CDCl₃): δ (ppm) 4.28 (t, 1H), 3.86 (m, 1H), 3.49 (dt, 2H), 1.6-1.95 (m, 8H), 1.56 (t, 2H), 1.41 (s, 9H).

(6) Step F: 1-{2-[(3S,4S)-4-(2,2-Dimethyl-propionyloxy)-3-methyl-piperidin-1-yl]-ethyl}-2-oxa-3-aza-bicyclo[2.2.2]octane-3-carboxylic acid tert-butyl ester (12)

(1S,4S)-1-(2-Hydroxy-ethyl)-2-oxa-3-aza-bicyclo[2.2.2]oct-5-ene-3-carboxylic acid tert-butyl ester (11) (620 mg, 2.41 mmol) is dissolved in 24 ml of propionitrile and after addition of amine 6 (480 mg, 2.41 mmol), cyanomethyl-trimethyl-phosphonium iodide (796 mg, 6 mmol) and diisopropyl ethyl amine (2 ml, 12 mmol) the mixture is stirred for

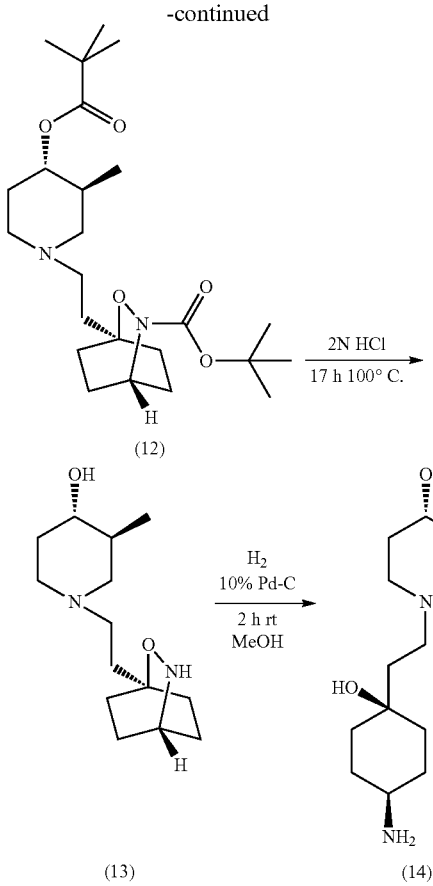

Synthesis of (3S,4S)-1-[2-(cis-4-Amino-1-hydroxy-cyclohexyl)-ethyl]-3-methyl-piperidin-4-ol (14)

(1) Step A: (Cyclohex-2-enesulfonyl)-benzene (7)

Bromocyclohexene (35.9 ml, 310.5 mmol) is dissolved in 1 l of DMF, cooled down to 0° C. and after addition of benzenesulfinic acid sodium salt (86.6 g, 527.8 mmol) the mixture is stirred for 17 h at room temperature. Then the mixture is evaporated under high vacuum. The residue is diluted with ether, washed with water, dried over $Na_2SO_4$ and evaporated under reduced pressure. The crude product is purified by Flash-chromatography (ethyl acetate/hexanes (1:9), 1 kg silicagel).

MS (ESI): 223.3 [M+H]⁺, 1H-NMR (CDCl₃): δ (ppm) 7.88 (d, 2H), 7.65 (d, 1H), 7.56 (dd, 2H), 6.1 (m, 1H), 6.8 (m, 1H), 3.75 (m, 1H), 1.4-2.0 (m, 6H).

(2) Step B: [2-(1-Benzenesulfonyl-cyclohex-2-enyl)-ethoxymethyl]-benzene (8)

Cyclohex-2-enesulfonyl-benzene (7) (10 g, 45 mmol) is dissolved in 450 ml of dry THF and cooled to −20° C. Then 1.6 M BuLi in Hexane (30.9 ml, 49.5 mmol) is added and stirred for 15 min. After addition of benzyl 2-bromoethylether (8.5 ml, 54 mmol) the mixture is stirred for 1 h at 0° C. Then the mixture is evaporated to dryness. The residue is treated with ice/1M HCl and extracted twice with ether. The combined organic layers are dried over $Na_2SO_4$ and evaporated under educed pressure. The product is used in the next step without further purification.

(7) Step G: (3S,4S)-3-Methyl-1-[2-(2-oxa-3-aza-bicyclo[2.2.2]oct-1-yl)-ethyl]-piperidin-4-ol hydrochloride (13)

(1S,4S)-1-{2-[(3S,4S)-4-(2,2-Dimethyl-propionyloxy)-3-methyl-piperidin-1-yl]-ethyl}-2-oxa-3-aza-bicyclo[2.2.2]oct-5-ene-3-carboxylic acid tert-butyl ester (12) (880 mg, 2 mmol) is dissolved in 20 ml of water and after addition of concentrated aqueous HCl (38%, 1.2 ml) the mixture is stirred for 16 h at 100° C. Then the mixture is evaporated to dryness. The residue s treated three times with methanol and evaporated under educed pressure. The residue is diluted with ethyl acetate, extracted with 2M $K_2CO_3$, dried over $Na_2SO_4$ and evaporated under reduced pressure. The product was used in the next step without further purification.

MS (ESI): 255 [M+H]$^+$, 1H-NMR (CDCl$_3$): δ (ppm) 12.18 (s, 2H), 3.73 (s, 1H), 3.3-3.4 (m, 2H), 3.15 (m, 2H), 2.99 (m, 2H), 2.9 (m, 1H), 2.59 (m, 2H), 2.1 (m, 2H), 1.99 (m, 2H), 1.6-1.9 (m, 8H), 0.9 (d, 3H).

(8) Step H: (3S,4S)-1-[2-(4-Amino-1-hydroxy-cyclohexyl)-ethyl]-3-methyl-piperidin-4-ol (14)

10% Pd—C (240 mg) is placed into a round-bottom flask under an argon atmosphere and covered with methanol. A solution of (3S,4S)-3-Methyl-1-[2-(2-oxa-3-aza-bicyclo[2.2.2]oct-1-yl)-ethyl]-piperidin-4-ol (13) (584 mg, 2.3 mmol) in 20 ml of methanol is added and the mixture is hydrogenated for 2 h at room temperature. Then the mixture is filtrated over celite and evaporated under reduced pressure. The product was used in the next step without further purification.

MS (ESI): 257 [M+H]$^+$, 1H-NMR (CDCl$_3$): δ (ppm) 4.67 (br, 1H), 4.5 (d, 1H), 2.88 (m, 1H), 2.78 (m, 1H), 2.76 (m, 1H), 2.41 (m, 1H), 2.3 (m, 2H), 1.84 (m, 1H), 1.7 (m, 1H), 1.52 (m, 6H), 1.42 (m, 3H), 1.32 (m, 4H), 1.3 (m, 2H), 0.86 (d, 3H).

Synthesis of the Alkyloxy Indole Building Blocks

The alkoxy indole building blocks are prepared according the reaction scheme outlined below.

Reaction Scheme 4:

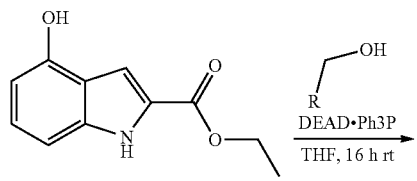

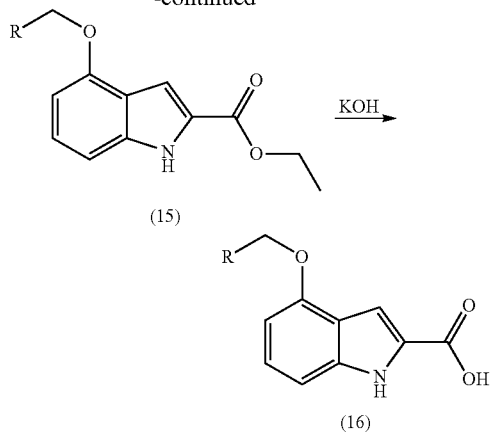

Synthesis of 4-Cyclobutylmethoxy-1H-indole-2-carboxylic acid (16a)

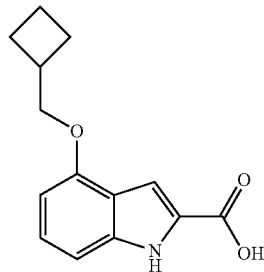 [SMILES: O=C(O)c1cc2c(OCC3CCC3)cccc2[nH]1]

(1) Step A: 4-Cyclobutylmethoxy-1H-indole-2-carboxylic acid ethyl ester (15a)

DEAD (2.1 ml, 13.65 mmol) is slowly added to a solution of 4-hydroxy-1H-indole-2-carboxylic acid ethyl ester (2 g, 9.75 mmol), triphenylphosphine (3.58 g, 13.65 mmol) and cyclobutyl-methanol (1.25 ml, 12.26 mmol) in 20 ml of THF, so that the temperature always remains below 30° C. Stirring is continued for 2 hours and the solvent is then evaporated. The crude residue is purified by chromatography (cyclohexane:EtOAc/95:5).

MS (ESI): 274.2 [M+H]$^+$, 1H-NMR (CDCl$_3$): δ (ppm) 8.83 (s, 1H), 7.35 (s, 1H), 7.21 (t, 1H), 6.98 (d, 1H), 6.49 (d, 1H), 4.4 (q, 2H), 4.07 (d, 2H), 2.85 (m, 1H), 2.17 (m, 2H), 1.95 (m, 4H), 1.42 (t, 3H).

(2) Step B: 4-Cyclobutylmethoxy-1H-indole-2-carboxylic acid (16a)

The 4-cyclobutylmethoxy-1H-indole-2-carboxylic acid ethyl ester (15a) obtained above is mixed with a 2M-solution of KOH in EtOH (16.9 ml, 33.8 mmol) and stirred for 24 hours. The solvent is then evaporated and the residue is partitioned between water and DCM. The water layer is acidified with HCl and extracted twice with EtOAc. The combined organic layers are washed with brine, dried over anhydrous sodium sulfate, filtered and evaporated to give a white powder.

MS (ESI): 246.3 [M+H]+, 1H-NMR (CDCl₃): δ (ppm) 11.74 (br. s, 1H), 7.14 (t, 1H), 7.03 (s, 1H), 6.99 (d, 1H), 6.51 (d, 1H), 4.05 (d, 2H), 2.8 (m, 1H), 2.11 (m, 2H), 1.93 (m, 4H).

Synthesis of 4-(Tetrahydro-furan-3-ylmethoxy)-1H-indole-2-carboxylic acid (16b)

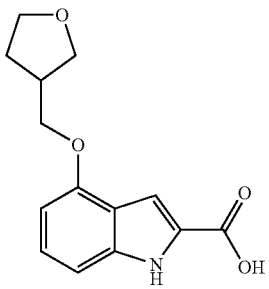 [SMILES: O=C(O)c1cc2c(OCC3CCOC3)cccc2[nH]1]

4-(Tetrahydro-furan-3-ylmethoxy)-1H-indole-2-carboxylic acid (16b) is synthesized analogous to 16a from 4-(tetrahydro-furan-3-yl)methanol and 4-hydroxy-1H-indole-2-carboxylic acid ethyl ester.

MS (ESI): 260.1 [M+H]+, 1H-NMR (DMSO-d₆): δ (ppm) 11.76 (br s, 1H), 7.14 (t, 1H), 7.03 (m, 2H), 6.52 (d, 1H), 4.05 (m, 2H), 3.83 (m, 2H), 3.69 (m, 1H), 3.6 (m, 1H), 2.74 (m, 1H), 2.05 (m, 1H), 1.73 (m, 1H).

Synthesis of 4-(furan-2-ylmethoxy)-1H-indole-2-carboxylic acid (16c)

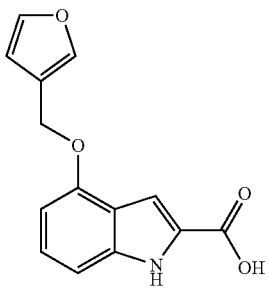 [SMILES: O=C(O)c1cc2c(OCc3ccoc3)cccc2[nH]1]

4-(Furan-3-ylmethoxy)-1H-indole-2-carboxylic acid (16c) is synthesized analogous to 16a from furan-3-yl-methanol and 4-hydroxy-1H-indole-2-carboxylic acid ethyl ester.

MS (ESI): 258.0 [M+H]+, 1H-NMR (DMSO-d₆): δ (ppm) 12.79 (br s, 1H), 11.71 (s, 1H), 7.81 (s, 1H), 7.67 (s, 1H), 7.13 (m, 1H), 7.01 (m, 2H), 6.62 (m, 2H), 5.07 (s, 2H).

Synthesis of 4-(2-Chloro-thiazol-4-ylmethoxy)-1H-indole-2-carboxylic acid (16d)

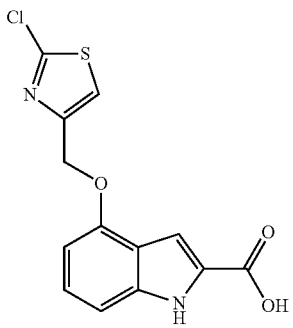 [SMILES: O=C(O)c1cc2c(OCc3csc(Cl)n3)cccc2[nH]1]

4-(2-Chloro-thiazol-4-ylmethoxy)-1H-indole-2-carboxylic acid (16d) is synthesized analogous to 16a from 4-(2-chloro-thiazol-4-yl)methanol and 4-hydroxy-1H-indole-2-carboxylic acid ethyl ester.

MS (ESI): 309, 311 [M+H]+, 1H-NMR (DMSO-d₆): δ (ppm) 12.9 (s, 1H), 11.8 (s, 1H), 7.85 (s, 1H), 7.15 (dd, 1H), 7.1 (m, 1H), 7.05 (d, 2H), 6.67 (d, 1H), 5.25 (s, 2H).

Synthesis of 4-(6-Methoxy-pyridin-3-ylmethoxy)-1H-indole-2-carboxylic acid (16e)

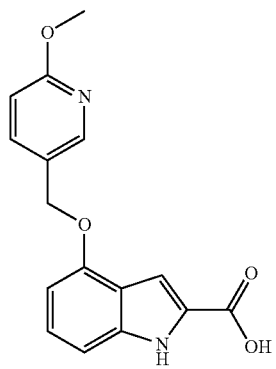 [SMILES: COc1ccc(COc2cccc3[nH]c(C(=O)O)cc23)cn1]

4-(6-Methoxy-pyridin-3-ylmethoxy)-1H-indole-2-carboxylic acid (16e) is synthesized analogous to 16a from 4-(6-methoxy-pyridin-3-yl)methanol and 4-hydroxy-1H-indole-2-carboxylic acid ethyl ester.

1H-NMR (DMSO-d₆): δ (ppm) 11.78 (s, 1H), 8.32 (s, 1H), 7.85 (d, 1H), 7.15 (t, 1H), 7.02 (m, 2H), 6.86 (d, 1H), 6.66 (d, 1H), 5.17 (s, 2H), 3.86 (s, 3H).

Synthesis of 4-(4-Oxo-4,5,6,7-tetrahydro-benzofuran-3-ylmethoxy)-1H-indole-2-carboxylic acid (16f)

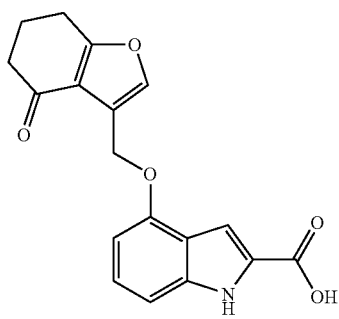 [SMILES: O=C(O)c1cc2c(OCc3coc4c3C(=O)CCC4)cccc2[nH]1]

4-(4-Oxo-4,5,6,7-tetrahydro-benzofuran-3-ylmethoxy)-1H-indole-2-carboxylic acid (16f) is synthesized analogous to 16a from 4-oxo-4,5,6,7-tetrahydro-benzofuran-3-yl-methanol and 4-hydroxy-1H-indole-2-carboxylic acid ethyl ester.

MS (ESI): 326 [M+H]+, 1H-NMR (DMSO-d₆): δ (ppm) 11.78 (br s, 1H), 7.88 (s, 1H), 7.16 (t, 1H), 7.11 (s, 1H), 7.03

(d, 1H), 6.59 (d, 1H), 5.21 (s, 2H), 3.3-3.9 (v br s, 1H), 2.91 (t, 2H), 2.45 (t, 2H), 2.11 (m, 2H).

Synthesis of 4-(6,6-Dimethyl-4-oxo-4,5,6,7-tetrahydro-benzofuran-3-ylmethoxy)-1H-indole-2-carboxylic acid (16g)

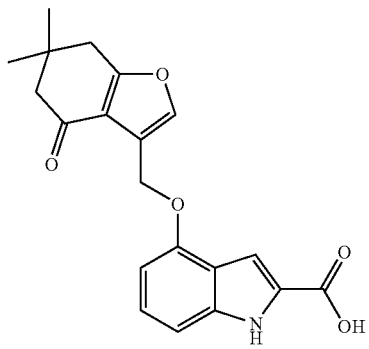 [SMILES: CC1(C)CC(=O)c2c(COc3cccc4[nH]c(C(=O)O)cc34)coc2C1]

4-(6,6-Dimethyl-4-oxo-4,5,6,7-tetrahydro-benzofuran-3-ylmethoxy)-1H-indole-2-carboxylic acid (16g) is synthesized analogous to 16a from 4-(6,6-dimethyl-4-oxo-4,5,6,7-tetrahydro-benzofuran-3-yl)methanol 19 (synthesis see below) and 4-hydroxy-1H-indole-2-carboxylic acid ethyl ester.

MS (ESI): 353 [M]$^+$, 1H-NMR (DMSO-d$_6$): δ (ppm) 12.8 (br s, 1H), 11.7 (s, 1H), 7.86 (s, 1H), 7.15 (dd, 1H), 7.08 (s, 1H), 7.02 (d, 1H), 6.57 (d, 1H), 5.2 (s, 2H), 2.8 (s, 2H), 2.36 (s, 2H), 1.06 (s, 6H).

Synthesis of 4-(6,6-Dimethyl-4-oxo-4,5,6,7-tetrahydro-benzofuran-3-ylmethanol (19)

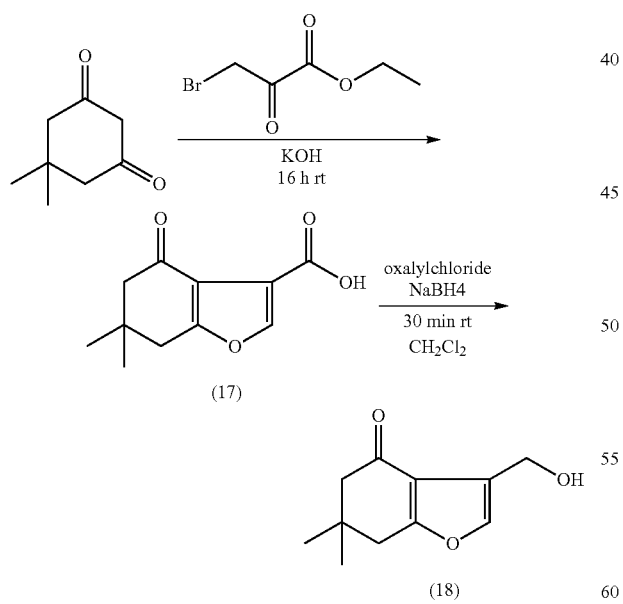

(1) Step A: 6,6-Dimethyl-4-oxo-4,5,6,7-tetrahydro-benzofuran-3-carboxylic acid (17)

5,5-Dimethyl-1,3-cyclohexandione is dissolved in 15 ml of methanol and cooled to 0° C. A solution of KOH (2 g, 35.7 mmol) in 15 ml of methanol is added drop wise. A solution of 3-bromo-2-oxo-propionic acid ethyl ester (4.7 ml, 37.5 mmol) in 15 ml of methanol is added drop wise. The mixture is allowed to warm up to room temperature and is stirred for 16 h. Then 15 ml of a 45% aqueous sodium hydroxide solution is added. After additional 4 h at room temperature, 25 ml of concentrated HCl is added. Methanol is evaporated slowly under reduced pressure whereas the product precipitates as light crystals. The product is filtrated off and washed with water.

MS (ESI): 209.0 [M+H]$^+$, 1H-NMR (DMSO-d$_6$): δ (ppm) 12.96 (br s, 1H), 8.38 (s, 1H), 2.86 (s, 2H), 2.49 (s, 2H), 1.07 (s, 6H).

(2) Step B: 6,6-Dimethyl-4-oxo-4,5,6,7-tetrahydro-benzofuran-3-ylmethanol (18)

6,6-Dimethyl-4-oxo-4,5,6,7-tetrahydro-benzofuran-3-carboxylic acid (17) (1 g, 4.8 mmol) is dissolved in 80 ml dichloromethane and after addition of 187 µl DMF (2.4 mmol) the mixture is cooled to 10-15° C. Oxalylchloride (619 ul, 7.2 mmol) is added drop wise and the mixture is stirred for 30 min at room temperature. The mixture is evaporated under reduced pressure, dissolved in THF and cooled to −55° C. A solution of NaBH$_4$ (1.3 g, 34.1 mmol) in 10 ml of DMF is added via syringe. The white suspension is allowed to stir for another 1.5 h at −55° C. 4 ml of acetic acid is added at this temperature and the mixture is poured into 150 ml of a 5% aqueous NaHCO$_3$ solution. The mixture is diluted with ethyl acetate and washed with brine. The crude product is purified by Flash-chromatography (ethyl acetate/hexanes (4:6), silicagel).

MS (ESI): 195.0 [M+H]$^+$, 1H-NMR (DMSO-d$_6$): δ (ppm) 7.47 (s, 1H), 4.95 (t, 1H), 4.5 (d, 2H), 2.76 (s, 2H), 2.32 (s, 2H), 1.06 (s, 6H).

Synthesis of 4-(6,6-Dimethyl-4-oxo-4,5,6,7-tetrahydro-benzofuran-3-ylmethoxy)-1H-indole-2-carboxylic acid (16h)

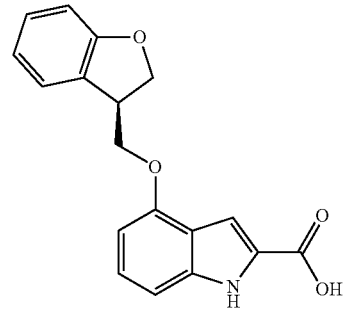 [SMILES: O=C(O)c1cc2c(OC[C@@H]3COc4ccccc43)cccc2[nH]1]

4-(6,6-Dimethyl-4-oxo-4,5,6,7-tetrahydro-benzofuran-3-ylmethoxy)-1H-indole-2-carboxylic acid (16h) is synthesized analogous to 16a from (R)-1-(2,3-dihydro-benzofuran-3-yl)-methanol and 4-hydroxy-1H-indole-2-carboxylic acid ethyl ester.

MS (ESI): 307.9 [M−H]⁻, 1H-NMR (DMSO-d₆): δ (ppm) 7.44 (d, 1H), 7.15 (m, 2H), 7.04 (m, 2H), 6.87 (t, 1H), 6.82 (d, 1H), 6.57 (d, 1H), 4.75 (t, 1H), 4.48 (dd, 1H), 4.3 (dd, 1H), 4.21 (dd, 1H), 4.02 (m, 1H).

Synthesis of 4-(6,6-Dimethyl-4-oxo-4,5,6,7-tetrahydro-benzofuran-3-ylmethoxy)-1H-indole-2-carboxylic acid (16i)

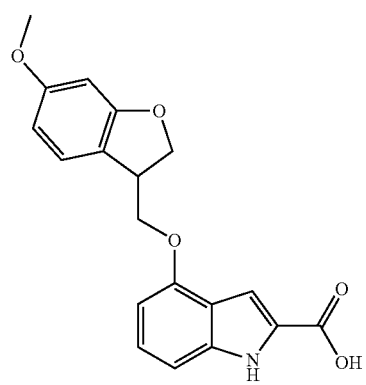 [SMILES: COc1ccc2c(c1)OCC2COc1cccc2[nH]c(C(=O)O)cc12]

4-(6,6-Dimethyl-4-oxo-4,5,6,7-tetrahydro-benzofuran-3-ylmethoxy)-1H-indole-2-carboxylic acid (16i) is synthesized analogous to 16a from (R,S)-(6-methoxy-2,3-dihydro-benzofuran-3-yl)-methanol 20 (synthesis see below) and 4-hydroxy-1H-indole-2-carboxylic acid ethyl ester.

MS (ESI): 339.9 [M+H]⁺, 1H-NMR (DMSO-d₆): δ (ppm) 11.8 (br s, 1H), 7.3 (d, 1H), 7.14 (t, 1H), 7.05 (m, 2H), 6.55 (d, 1H), 6.45 (m, 2H), 4.75 (t, 1H), 4.5 (dd, 1H), 4.25 (m, 1H), 4.15 (m, 1H), 3.93 (m, 1H), 3.7 (s, 3H).

Synthesis of (R,S)-(6-methoxy-2,3-dihydro-benzofuran-3-yl)-methanol (23)

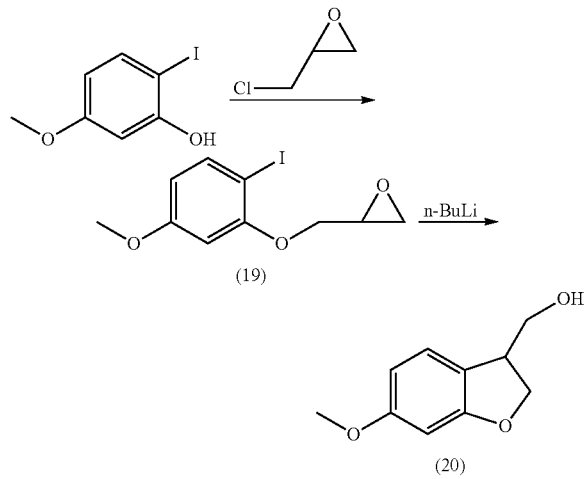

(1) Step A: (R,S)-2-(2-Iodo-5-methoxy-phenoxymethyl)-oxirane (19)

2-Iodo-5-methoxy-phenol (2 g, 8 mmol) is dissolved in 15 ml of DMF. Caesium carbonate (3.9 g, 12 mmol) and 2-chloromethyl-oxirane (0.94 ml, 12 mmol) is added and the mixture is stirred for 60 hours. The reaction is then treated with 10 ml of 2N NaOH and extracted with diethyl ether. The ether layer is washed with 1N-NaOH, water and brine, dried over sodium sulfate and evaporated. The crude oil is used without further purification in the next step.

MS (ESI): 306.8 [M+H]⁺, 1H-NMR (CDCl₃): δ (ppm) 7.56 (d, 1H), 6.4 (d, 1H), 6.28 (dd, 1H), 4.2 (dd, 1H), 3.97 (dd, 1H), 3.72 (s, 3H), 3.33 (m, 1H), 2.85 (m, 2H).

(2) Step B: (R)-1-(2,3-dihydro-benzofuran-3-yl)-methanol (20)

The crude oxirane 19 from above (2.4 g, 7.84 mmol) is dissolved in 50 ml of THF and cooled to −78° C. in a dry-ice bath. At this temperature, n-BuLi (1.6M in hexane, 4.9 ml, 7.84 mmol) is added drop wise. The mixture is then stirred for one hour and allowed to warm up to 0° C. After careful hydrolysis and extraction with EtOAc the crude is purified by Flash-chromatography (ethyl acetate/hexanes (from 5:95 to 25:75), silicagel).

MS (ESI): 180.9 [M+H]⁺, 1H-NMR (CDCl₃): δ (ppm) 7.1 (d, 1H), 6.46 (d, 1H), 6.42 (s, 1H), 4.67 (dd, 1H), 4.52 (dd, 1H), 3.79 (s, 3H), 3.6 (m, 1H), 1.65 (br s, 1H).

Synthesis of 4-[2-(2-methoxy-phenyl)-ethoxy]-1H-indole-2-carboxylic acid (16j)

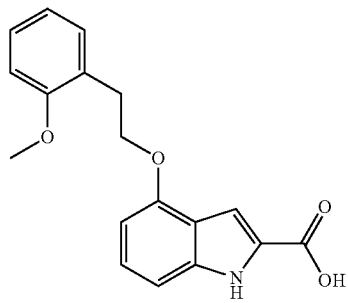 [SMILES: COc1ccccc1CCOc1cccc2[nH]c(C(=O)O)cc12]

4-[2-(2-Methoxy-phenyl)-ethoxy]-1H-indole-2-carboxylic acid (16j) is synthesized analogous to 16a from 2-(2-methoxy-phenyl)-ethanol and 4-hydroxy-1H-indole-2-carboxylic acid ethyl ester.

MS (ESI): 312 [M+H]⁺, 1H-NMR (DMSO-d₆): δ (ppm) 10.75 (br, 1H), 7.28 (dd, 1H), 7.20 (ddd, 1H), 6.97 (d, 1H), 6.83-6.92 (m, 3H), 6.47 (s, 1H), 6.38 (dd, 1H), 4.17 (t, 2H), 3.81 (s, 3H), 3.07 (t, 2H).

Synthesis of 4-[2-(3-methoxy-phenyl)-ethoxy]-1H-indole-2-carboxylic acid (16k)

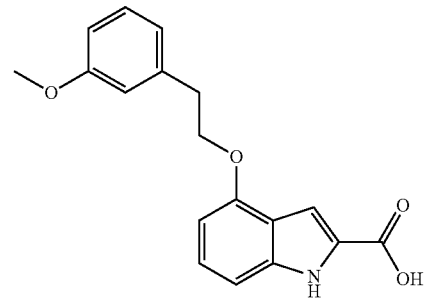 [SMILES: COc1cccc(CCOc2cccc3[nH]c(C(=O)O)cc23)c1]

4-[2-(3-Methoxy-phenyl)-ethoxy]-1H-indole-2-carboxylic acid (16k) is synthesized analogous to 16a from 2-(3-methoxy-phenyl)-ethanol and 4-hydroxy-1H-indole-2-carboxylic acid ethyl ester.

MS (ESI): 312 [M+H]+, 1H-NMR (DMSO-d6): δ (ppm) 12.8 (br, 1H), 11.69 (s, 1H), 7.22 (dd, 1H), 7.11 (dd, 1H), 6.91-6.99 (m, 2H), 6.79 (m, 1H), 6.50 (d, 1H), 4.27 (t, 2H), 3.74 (s, 3H), 3.06 (t, 2H).

Synthesis of 4-[2-(4-methoxy-phenyl)-ethoxy]-1H-indole-2-carboxylic acid (16l)

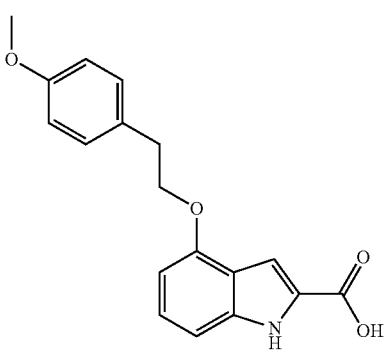 [SMILES: COc1ccc(CCOc2cccc3[nH]c(C(=O)O)cc23)cc1]

4-[2-(4-Methoxy-phenyl)-ethoxy]-1H-indole-2-carboxylic acid (16l) is synthesized analogous to 16a from 2-(4-methoxy-phenyl)-ethanol and 4-hydroxy-1H-indole-2-carboxylic acid ethyl ester.

MS (ESI): 312 [M+H]+, 1H-NMR (DMSO-d6): δ (ppm) 12.85 (br, 1H), 11.69 (s, 1H), 7.28 (d, 2H), 7.1 (dd, 1H), 6.96-6.95 (m, 2H), 6.87 (d, 2H), 6.50 (d, 1H), 4.23 (t, 2H), 3.72 (s, 3H), 3.04 (t, 2H).

Synthesis of 4-[2-(2-methoxy-pyridin-3-yl)-ethoxy]-1H-indole-2-carboxylic acid (16m)

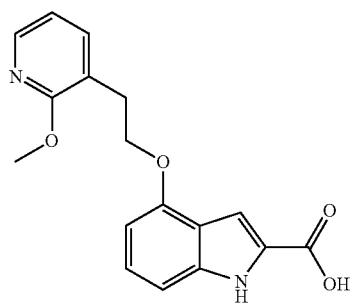 [SMILES: COc1ncccc1CCOc1cccc2[nH]c(C(=O)O)cc12]

4-[2-(2-Methoxy-pyridin-3-yl)-ethoxy]-1H-indole-2-carboxylic acid (16m) is synthesized analogous to 16a from 4-[2-(2-methoxy-pyridin-3-yl)-ethanol and 4-hydroxy-1H-indole-2-carboxylic acid ethyl ester.

MS (ESI): 313.2 [M+H]+, 1H-NMR (DMSO-d6): δ (ppm) 11.74 (s, 1H), 8.06 (d, 1H), 7.71 (d, 1H), 7.13 (t, 1H), 6.97 (m, 2H), 6.55 (d, 1H), 4.26 (t, 2H), 3.9 (s, 3H), 3.07 (t, 2H).

Synthesis of 4-[2-(6-methoxy-pyridin-3-yl)-ethoxy]-1H-indole-2-carboxylic acid (16n)

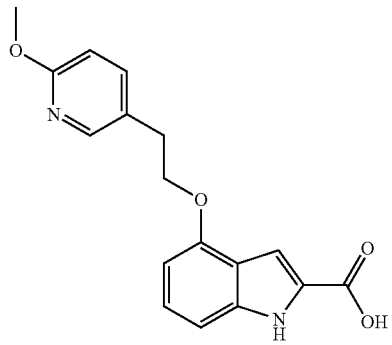 [SMILES: COc1ccc(CCOc2cccc3[nH]c(C(=O)O)cc23)cn1]

4-[2-(6-Methoxy-pyridin-3-yl)-ethoxy]-1H-indole-2-carboxylic acid (16n) is synthesized analogous to 16a from 4-[2-(6-methoxy-pyridin-3-yl)-ethanol and 4-hydroxy-1H-indole-2-carboxylic acid ethyl ester.

MS (ESI): 313.0 [M+H]+.

Synthesis of 4-[2-(6-methoxy-benzofuran-3-yl)-ethoxy]-1H-indole-2-carboxylic acid (16o)

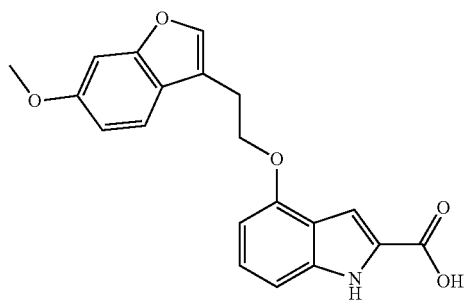 [SMILES: COc1ccc2c(CCOc3cccc4[nH]c(C(=O)O)cc34)coc2c1]

4-[2-(6-methoxy-benzofuran-3-yl)-ethoxy]-1H-indole-2-carboxylic acid (16o) is synthesized analogous to 16a from 4-[2-(6-methoxy-benzofuran-3-yl)-ethanol 21 (synthesis see below) and 4-hydroxy-1H-indole-2-carboxylic acid ethyl ester.

1H-NMR (DMSO-d6): δ (ppm) 11.7 (s, 1H), 7.82 (s, 1H), 7.65 (d, 1H), 7.17 (d, 1H), 7.12 (t, 1H), 7.0 (m, 2H), 6.89 (dd, 1H), 6.55 (dd, 1H), 4.34 (m, 2H), 3.8 (s, 3H), 3.16 (m, 2H).

Synthesis of 4-[2-(6-methoxy-benzofuran-3-yl)-ethanol (21)

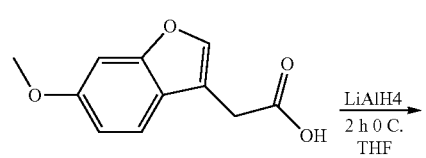

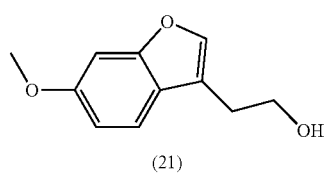

(21)

A solution of (6-methoxy-benzofuran-3-yl)-acetic acid (10.16 g, 49.3 mmol) in 500 ml of THF is cooled in an ice-bath. To this solution is added LAH (1M in THF, 49.3 ml, 49.3 mmol) and stirring is continued for 1 hour. The reaction mixture is then poured onto ice cold 1N HCl and extracted 3-times with EtOAc. The combined organic layers are dried and evaporated.

1H-NMR (CDCl$_3$): δ (ppm) 7.43 (s, 1H), 7.42 (d, 1H), 7.01 (d, 1H), 6.88 (dd, 1H), 3.91 (t, 2H), 3.85 (s, 3H), 2.91 (t, 2H), 1.6 (v br s, 1H).

Synthesis of the Benzofurane Building Blocks

The benzofurane building block 26 is prepared according the reaction scheme outlined below.

Reaction Scheme 5:

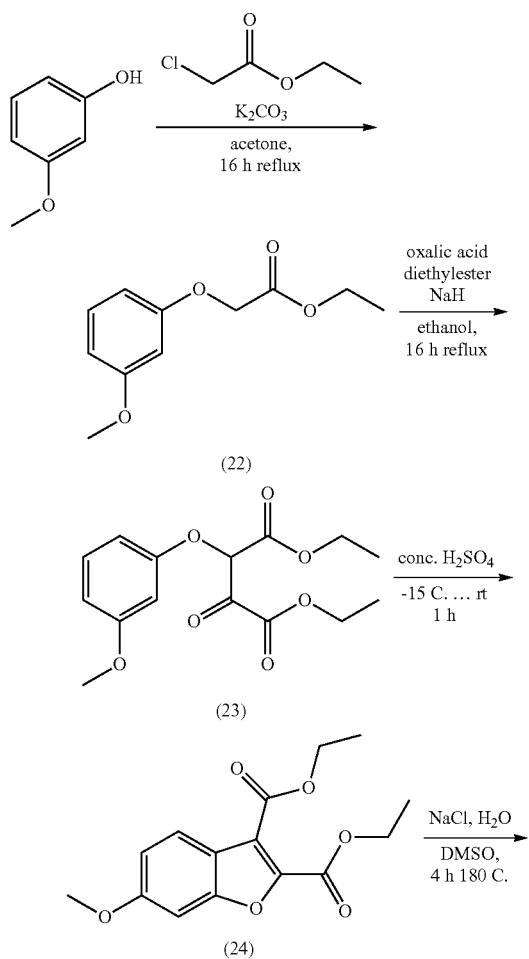

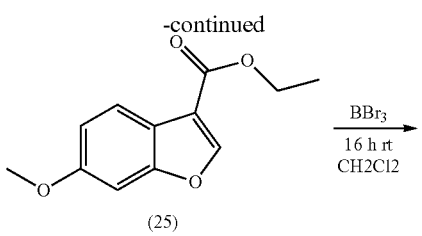

(25)

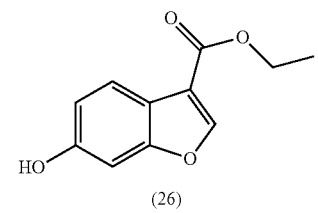

(26)

Synthesis of 6-hydroxy-benzofuran-3-carboxylic acid ethyl ester (26)

(1) Step A: (3-Methoxy-phenoxy)-acetic acid ethyl ester (22)

3-Methoxy-phenol (43.4 ml, 400 mmol) is dissolved in acetone (800 ml) and after addition of chloro-acetic acid ethyl ester (42.6 ml, 400 mmol) and K$_2$CO$_3$ (111 g, 800 mmol) the mixture is refluxed for 22 h. After cooling down to 0° C., the mixture is filtrated and the filtrate is evaporated under reduced pressure. The residue is diluted in ethyl acetate, cooled to 0° C. and washed with aqueous NaOH solution. The organic layer is dried over sodium sulfate and evaporated under reduced pressure.

MS (ESI): 211.54 [M+H]$^+$, 1H-NMR (DMSO-d$_6$): δ (ppm) 7.20 (dd, 1H), 6.56 (dd, 1H), 6.50 (m, 2H), 4.77 (s, 2H), 4.19 (q, 2H), 3.75 (s, 3H), 1.23 (t, 3H).

(2) Step B: 2-(3-Methoxy-phenoxy)-3-oxo-succinic acid diethyl ester (23)

Sodium ethoxide (32.5 g, 454 mmol) is covered with 1 l of dry diethyl ether. Oxalic acid diethyl ester (55.2 ml, 416 mmol) is added drop wise within 20 min. After 30 min stirring at room temperature, the mixture is heated to reflux. A solution of (3-methoxy-phenoxy)-acetic acid ethyl ester (22) (79.5 g, 378 mmol) in 80 ml of dry diethyl ether is added drop wise within 30 min and the mixture is allowed to reflux for 1 hour. After cooling down to room temperature, the reaction mixture is poured on 2M HCl (400 ml)/ice (400 g) and extracted with diethyl ether. The organic layers are dried over sodium sulfate, filtrated and evaporated.

MS (ESI): 310 [M]$^+$, 1H-NMR (DMSO-d$_6$): δ (ppm) 7.15-7.2 (m, 1H), 6.5-6.6 (m, 1H), 6.4-6.5 (m, 1H), 4.25 (m, 4H), 4.0-4.2 (m, 3H), 3.71 (s, 3H), 1.05-1.3 (m, 6H).

(3) Step C: 6-Methoxy-benzofuran-2,3-dicarboxylic acid diethyl ester (24)

2-(3-Methoxy-phenoxy)-3-oxo-succinic acid diethyl ester (23) (60 g, 193.4 mmol) is dissolved in 32 ml of cooled (−15° C.) conc. sulfuric acid and stirred for 3 h whereas the reaction mixture slowly warmed up to room temperature. Then the mixture is poured onto 1 kg of ice and extracted with diethyl ether. The organic layers are washed with brine, dried over sodium sulfate, filtrated and evaporated. The crude product is purified by Flash-chromatography (silica gel, ethyl acetate/hexanes 1:9).

MS (ESI): 293.67 [M+H]$^+$, 1H-NMR (DMSO-d$_6$): δ (ppm) 7.7 (d, 1H), 7.39 (d, 1H), 7.06 (dd, 1H), 4.38 (q, 2H), 4.36 (q, 2H), 3.64 (s, 3H), 1.34 (t, 3H), 1.32 (t, 3H).

(4) Step D: 6-Methoxy-benzofuran-3-carboxylic acid ethyl ester (25)

6-Methoxy-benzofuran-2,3-dicarboxylic acid diethyl ester (24) (27 g, 92 mmol) is dissolved in 200 ml of a DMSO and the mixture is heated to 170° C. Then sodium chloride (10.7 g, 184 mmol) and water (3.3 ml) are added and the mixture is stirred for 2 h at 160° C. (temperature of reaction mixture). Then the mixture is allowed to cool down and evaporated at high vacuum. The residue is dissolved in ethyl acetate, washed with water and brine and dried over sodium sulfate. Evaporation gave an brown solid, which is further purified by Flash-chromatography (silica gel, ethyl acetate/hexanes 3:7).

MS (ESI): 221 [M+H]$^+$, 1H-NMR (DMSO-d$_6$): δ (ppm) 8.6 (s, 1H), 7.79 (d, 1H), 7.3 (d, 1H), 7.01 (dd, 1H), 4.32 (q, 2H), 3.81 (s, 3H), 1.34 (t, 3H).

(5) Step E: 6-Hydroxy-benzofuran-3-carboxylic acid ethyl ester (26)

6-Methoxy-benzofuran-3-carboxylic acid ethyl ester (25) (9.3 g, 42 mmol) is dissolved in 80 ml of dichloromethane and cooled to 0° C. 1M solution of BBr$_3$ in dichloromethane (84.5 ml, 84.5 mmol) is added and the mixture is stirred at rt for 2 h. The mixture is poured on ice water and neutralized with sodium hydrogen carbonate. The organic layer is dried over sodium D sulfate, filtrated and evaporated under reduced pressure.

MS (ESI): 205 [M−H]$^-$, 1H-NMR (DMSO-d$_6$): δ (ppm) 9.74 (br, 1H), 8.50 (s, 1H), 7.69 (d, 1H), 6.98 (d, 1H), 6.86 (dd, 1H), 4.31 (q, 2H), 1.32 (t, 3H).

Synthesis of the Benzofuranyl-Methoxy Indol Building Blocks

The alkoxy indol building blocks are prepared according the reaction scheme outlined below.

Reaction Scheme 6:

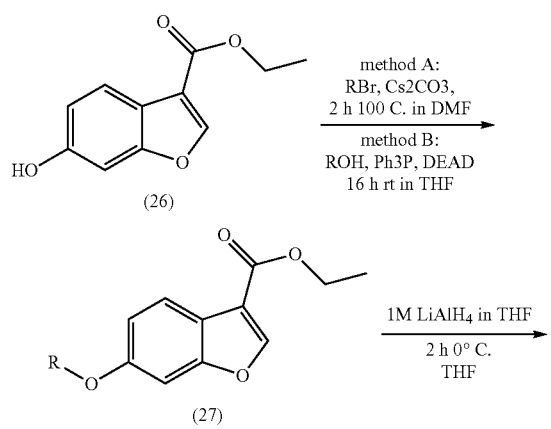

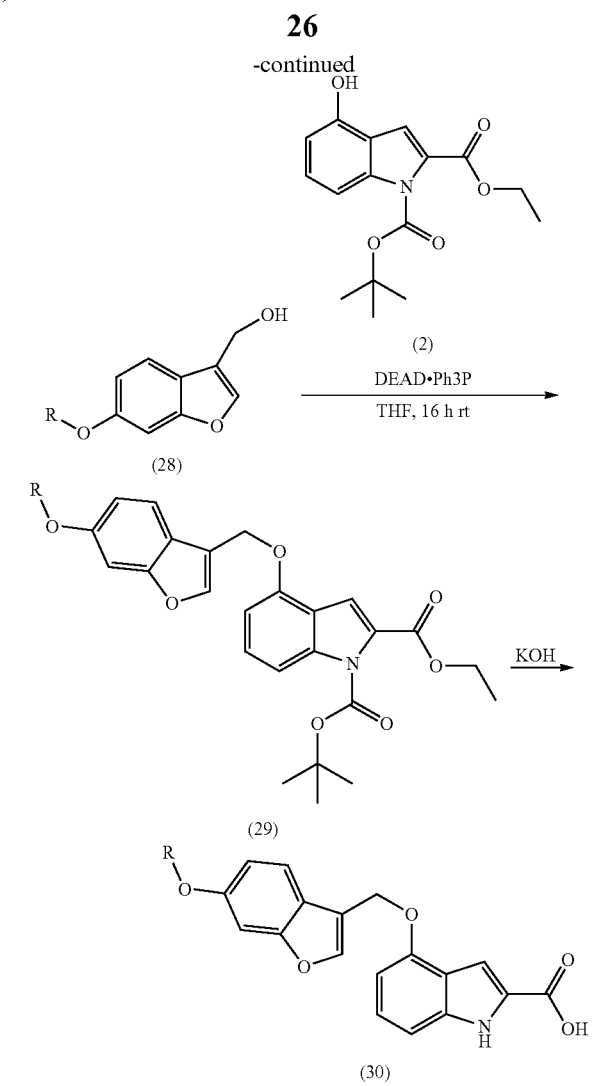

Synthesis of 4-(6-Ethoxy-benzofuran-3-ylmethoxy)-1H-indole-2-carboxylic acid (30a) (method A)

(1) Step A: 6-Ethoxy-benzofuran-3-carboxylic acid ethyl ester (27a)

6-Hydroxy-benzofuran-3-carboxylic acid ethyl ester (26) (8 g, 39 mmol) is dissolved in 80 ml of DMF and after addition of bromoethane (5.8 ml, 78 mmol) and Cs$_2$CO$_3$ (15.2 g, 46.6 mmol) the mixture is stirred for 2 h at 100° C. After evaporation of the mixture at high vacuum, the residue is dissolved in ethyl acetate, washed with water and with brine, dried over sodium sulfate and evaporated under reduced pressure. The yellow solid is used in the next step without further purification.

MS (ESI): 235 [M+H]+, 1H-NMR (DMSO-d$_6$): δ (ppm) 8.58 (s, 1H), 7.77 (d, 1H), 7.27 (s, 1H), 6.99 (d, 1H), 4.31 (q, 2H), 4.07 (q, 2H), 1.35 (t, 3H), 1.33 (t, 3H).

(2) Step B: (6-Ethoxy-benzofuran-3-yl)-methanol (28a)

1M LiAlH$_4$-solution in THF (47.6 ml, 47.6 mmol) is diluted with 200 ml of THF and cooled to 0° C. 6-Ethoxy-benzofuran-3-carboxylic acid ethyl ester (27a) (5.6 g, 23.8 mmol) is dissolved in 100 ml of THF and added drop wise within 30 min. After completed addition the mixture is allowed to stir at 0° C. for 2 h. Then the reaction mixture is cooled to −15° C. and 10 ml of a 1M NaOH solution is added very slowly. Then the mixture is filtrated over celite, washed with THF and evaporated under reduced pressure.

MS (ESI): 193 [M+H]+, 1H-NMR (DMSO-d$_6$): δ (ppm) 7.7 (s, 1H), 7.5 (d, 1H), 7.12 (d, 1H), 7.85 (dd, 1H), 5.1 (br s, 1H), 4.58 (s, 2H), 4.05 (q, 2H), 1.35 (t, 3H).

(3) Step C: 4-(6-Ethoxy-benzofuran-3-ylmethoxy)-indole-1,2-dicarboxylic acid 1-tert-butyl ester 2-ethyl ester (29a)

4-Hydroxy-indole-1,2-dicarboxylic acid 1-tert-butyl ester 2-ethyl ester (2) (5.2 g, 17.2 mmol), (6-ethoxy-benzofuran-3-yl)-methanol (28a) (3.3 g, 17.2 mmol) and triphenylphosphine (5.4 g, 20.6 mmol) are dissolved in 30 ml of THF and cooled to 0° C. Then 40% ethyl azodicarboxylate solution in THF (9 ml, 20.6 mmol) is added drop wise. After completed addition the mixture is stirred for 16 h (TLC control) at rt. Then the mixture is evaporated under reduced pressure. The residue is diluted with ethyl acetate, washed sat. NaHCO$_3$- and NaCl-solution, and dried over Na$_2$SO$_4$. The crude product is purified by Flash-chromatography (ethyl acetate/hexanes (1:9), silicagel).

MS (ESI): 480 [M+H]+, 1H-NMR (DMSO-d$_6$): δ (ppm) 8.04 (s, 1H), 7.55 (d, 1H), 7.52 (d, 1H), 7.39 (dd, 1H), 7.17 (s, 1H), 7.17 (s, 1H), 7.03 (d, 1H), 6.88 (d, 1H), 5.38 (s, 2H), 4.28 (q, 2H), 4.0-4.1 (m, 2H), 1.55 (s, 9H), 1.34 (t, 3H), 1.29 (t, 3H).

(4) Step D: 4-(6-Ethoxy-benzofuran-3-ylmethoxy)-1H-indole-2-carboxylic acid (30a)

4-(6-Ethoxy-benzofuran-3-ylmethoxy)-indole-1,2-dicarboxylic acid 1-tert-butyl ester 2-ethyl ester (29a) (7.5 g, 15.6 mmol) is dissolved in 150 ml of a 1:1:1 mixture of THF, ethanol and water. And after addition of KOH pellets (4.4 g, 78.2 mmol) the mixture is stirred for 2 h (TLC control) at 85° C. Then the organic solvent is removed under reduced pressure. The residue is cooled to 0° C. and treated with 2M HCl. The crude product is filtered off and dried under high vacuum. The crude product is recrystallized from ethyl acetate.

MS (ESI): 352 [M+H]+, 1H-NMR (DMSO-d$_6$): δ (ppm) 12.81 (br s, 1H), 11.72 (s, 1H), 8.01 (s, 1H), 7.56 (d, 1H), 7.17 (s, 1H), 7.14 (dd, 1H), 7.02 (m, 2H), 6.89 (d, 1H), 6.71 (d, 1H), 5.33 (s, 2H), 4.05 (q, 2H), 1.34 (t, 3H).

Synthesis of 4-(6-cyclopropylmethoxy-benzofuran-3-ylmethoxy)-1H-indole-2-carboxylic acid (30b) (method A)

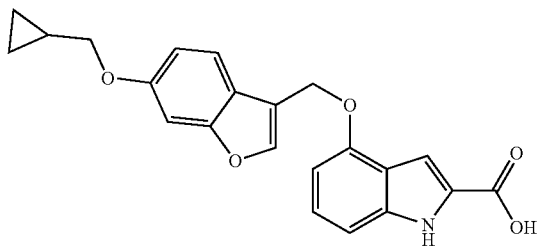 [SMILES: O=C(O)c1cc2c(OCc3coc4cc(OCC5CC5)ccc34)cccc2[nH]1]

4-(6-cyclopropylmethoxy-benzofuran-3-ylmethoxy)-1H-indole-2-carboxylic acid (30b) is synthesized analogous to 30a from 6-Hydroxy-benzofuran-3-carboxylic acid ethyl ester (26) and bromomethyl cyclopropane.

MS (ESI): 376 [M−H]−, 1H-NMR (DMSO-d$_6$): δ (ppm) 12.82 (br s, 1H), 11.72 (s, 1H), 8.01 (s, 1H), 7.57 (d, 1H), 7.16 (d, 1H), 7.14 (d, 1H), 7.02 (m, 2H), 6.91 (dd, 1H), 6.71 (d, 1H), 5.34 (s, 2H), 3.85 (d, 2H), 1.24 (m, 1H), 0.58 (m, 2H), 0.34 (m, 2H).

Synthesis of 4-[6-(2-Ethoxy-ethoxy)-benzofuran-3-ylmethoxy]-1H-indole-2-carboxylic acid (30c) (method A)

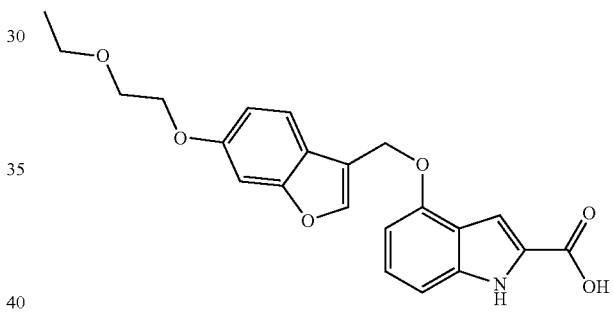

4-[6-(2-Ethoxy-ethoxy)-benzofuran-3-ylmethoxy]-1H-indole-2-carboxylic acid (30c) is synthesized analogous to 30a from 6-hydroxy-benzofuran-3-carboxylic acid ethyl ester (26) and 2-bromoethyl ethyl ether.

MS (ESI): 394 [M−H]−, 1H-NMR (DMSO-d$_6$): δ (ppm) 12.82 (br s, 1H), 11.73 (s, 1H), 8.03 (s, 1H), 7.57 (d, 1H), 7.21 (d, 1H), 7.15 (dd, 1H), 7.02 (s, 1H), 7.01 (d, 1H), 6.92 (dd, 1H), 6.72 (d, 1H), 5.35 (s, 2H), 4.12 (dd, 2H), 3.71 (dd, 2H), 3.50 (q, 2H), 1.13 (t, 3H).

Synthesis of 4-[6-(2-Methoxy-1-methyl-ethoxy)-benzofuran-3-ylmethoxy]-1H-indole-2-carboxylic acid (30d) (method B)

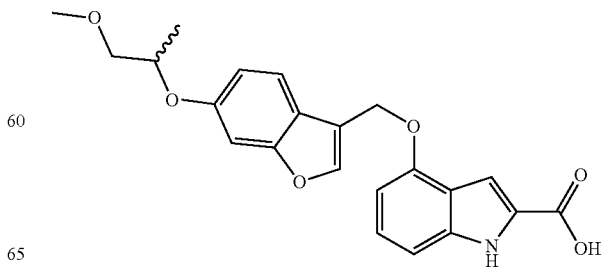

(1) Step A: 6-(2-Methoxy-1-methyl-ethoxy)-benzofuran-3-carboxylic acid ethyl ester (27d)

6-Hydroxy-benzofuran-3-carboxylic acid ethyl ester (26) (0.5 g, 2.4 mmol) is dissolved in 24 ml of dry THF and after addition of 1-methoxy-2-propanol (262 mg, 2.9 mmol) and triphenylphosphine (763 mg, 2.9 mmol) the mixture is cooled to 0° C. Then a 40% solution of ethyl azodicarboxylate in toluene (1.3 ml, 2.9 mmol) is added drop wise and the reaction mixture is stirred for 16 h at room temperature. Subsequently, the mixture is evaporated under reduced pressure, and the crude product is purified by Flash-chromatography (silica gel, ethyl acetate/hexanes 1:9) to yield a colourless oil.

MS (ESI): 279 [M+H]$^+$, 1H-NMR (DMSO-d$_6$): δ (ppm) 8.58 (s, 1H), 7.77 (d, 1H), 7.33 (d, 1H), 6.99 (dd, 1H), 4.67 (m, 1H), 4.31 (q, 2H), 3.48 (m, 2H), 3.28 (d, 3H), 1.33 (t, 3H), 1.23 (d, 3H).

Step B through D are performed according to the synthesis of 30a.

4-[6-(2-Methoxy-1-methyl-ethoxy)-benzofuran-3-ylmethoxy]-1H-indole-2-carboxylic acid (30d) MS (ESI): 396.64 [M+H]$^+$.

Synthesis of 4-[6-(2-Isopropoxy-ethoxy)-benzofuran-3-ylmethoxy]-1H-indole-2-carboxylic acid (30e) (method B)

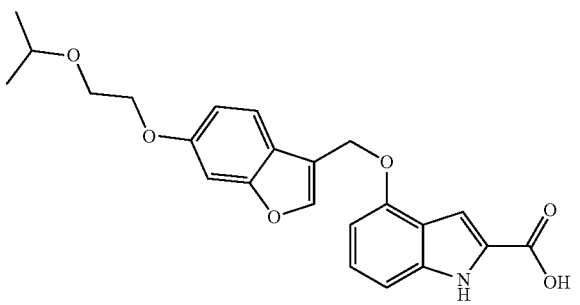 [SMILES: CC(C)OCCOc1ccc2c(COc3cccc4[nH]c(C(=O)O)cc34)coc2c1]

4-[6-(2-Isopropoxy-ethoxy)-benzofuran-3-ylmethoxy]-1H-indole-2-carboxylic acid (30e) is synthesized analogous to 30d from 6-hydroxy-benzofuran-3-carboxylic acid ethyl ester (26) and 2-isopropoxyethanol.

MS (ESI): 408 [M−H]$^−$, 1H-NMR (DMSO-d$_6$): δ (ppm) 12.8 (br s, 1H), 11.73 (s, 1H), 8.03 (s, 1H), 7.56 (d, 1H), 7.21 (s, 1H), 7.15 (dd, 1H), 7.03 (s, 1H), 7.0 (m, 1H), 6.93 (dd, 1H), 6.73 (d, 1H), 5.35 (s, 2H), 4.1 (t, 2H), 3.7 (t, 2H), 3.63 (m, 1H), 1.11 (s, 6H).

Synthesis of 4-[6-(3-Methoxy-propoxy)-benzofuran-3-ylmethoxy]-1H-indole-2-carboxylic acid (30f) (method B)

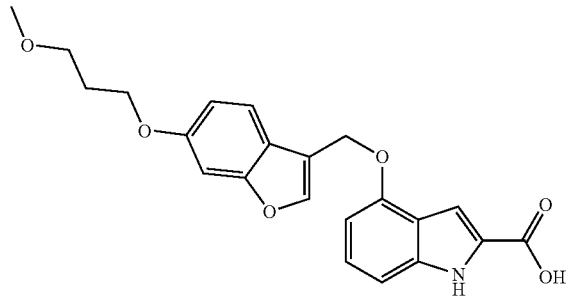 [SMILES: COCCCOc1ccc2c(COc3cccc4[nH]c(C(=O)O)cc34)coc2c1]

4-[6-(3-Methoxy-propoxy)-benzofuran-3-ylmethoxy]-1H-indole-2-carboxylic acid (30f) is synthesized analogous to 30d from 6-hydroxy-benzofuran-3-carboxylic acid ethyl ester (26) and 3-methoxy-1-propanol.

Synthesis of 4-[6-(3-ethoxy-propoxy)-benzofuran-3-ylmethoxy]-1H-indole-2-carboxylic acid (30g) (method B)

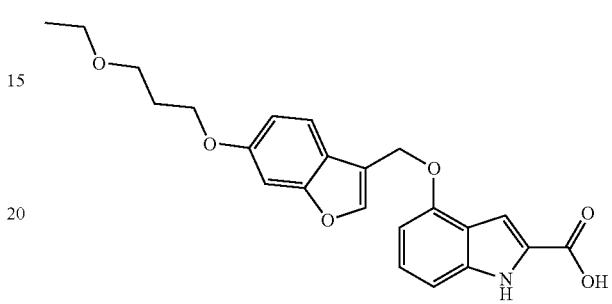

4-[6-(3-ethoxy-propoxy)-benzofuran-3-ylmethoxy]-1H-indole-2-carboxylic acid (30g) is synthesized analogous to 30d from 6-hydroxy-benzofuran-3-carboxylic acid ethyl ester (26) and 3-ethoxy-1-propanol.

Synthesis of 4-{6-[(S)-(tetrahydro-furan-3-yl)oxy]-benzofuran-3-ylmethoxy}-1H-indole-2-carboxylic acid (30h) (method B)

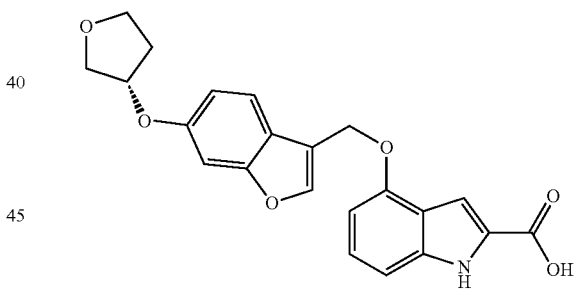

4-{6-[(S)-(Tetrahydro-furan-3-yl)oxy]-benzofuran-3-ylmethoxy}-1H-indole-2-carboxylic acid (30h) is synthesized analogous to 30d from 6-hydroxy-benzofuran-3-carboxylic acid ethyl ester (26) and (S)-(−)-3-hydroxytetrahydrofurane.

MS (ESI): 392 [M−H]$^−$, 1H-NMR (DMSO-d$_6$): δ (ppm) 12.79 (br s, 1H), 11.72 (s, 1H), 8.03 (s, 1H), 7.58 (d, 1H), 7.19 (d, 1H), 7.14 (dd, 1H), 7.01 (s, 1H), 7.0 (m, 1H), 6.89 (dd, 1H), 6.71 (d, 1H), 5.34 (s, 2H), 5.07 (m, 1H), 3.7-3.95 (m, 4H), 2.22 (m, 1H), 1.99 (m, 1H).

Synthesis of the indole-2-carboxamides

The indole-2-carboxamides are generally prepared by a TBTU-mediated coupling of appropriately substituted indole-2-carboxylic acids with the corresponding amines in the presence of Hünig's base (Reaction Scheme 7).

Reaction Scheme 7:

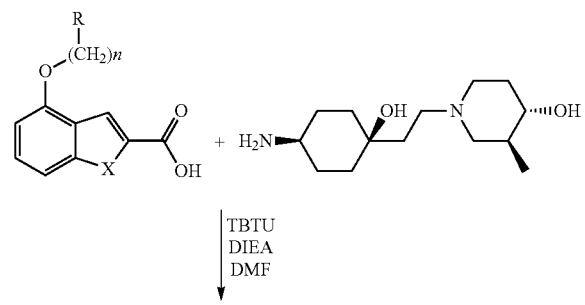

TBTU
DIEA
DMF

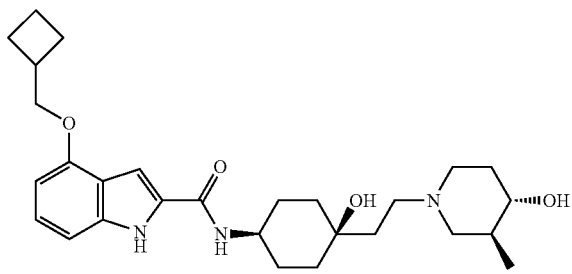 [SMILES: C[C@H]1CN(CC[C@]2(O)CC[C@@H](NC(=O)c3cc4c(OCC5CCC5)cccc4[nH]3)CC2)CC[C@@H]1O]

An illustrative example is given below.

Example 1

4-Cyclobutylmethoxy-1H-indole-2-carboxylic acid {4-hydroxy-4-[2-((3S,4S)-4-hydroxy-3-methyl-piperidin-1-yl)-ethyl]-cyclohexyl}-amide A solution of 4-cyclobutylmethoxy-1H-indole-2-carboxylic acid (16a) (140 mg, 0.383 mmol), (3S,4S)-1-[2-(4-amino-1-hydroxy-cyclohexyl)-ethyl]-3-methyl-piperidin-4-ol (14) (103 mg, 0.421 mmol) and DIEA (0.263 ml, 1.532 mmol) in 5 ml of DMF is treated with solid TBTU (139 mg, 0.421 mmol). The mixture is stirred for 2 h at rt and then evaporated. The crude residue is dissolved in EtOAc and extracted with 1M-HCl. The aqueous layer is separated, its pH adjusted to 14 and extracted 3-times with DCM. The organic layers are dried over sodium sulphate and evaporated. The crude product is then purified by chromatography on silicagel using methanol and DCM (saturated with ammonia) from 1:99 to 5:95.

The formation of the hydrochlorides can be achieved by treatment of a solution of the free base in DCM or acetone with 2M HCl in methanol at 0° C.

MS (ESI): 484 [M+H]$^+$, 1H-NMR (DMSO-d$_6$): δ (ppm) 11.46 (s, 1H), 8.26 (d, 1H), 7.25 (s, 1H), 7.04 (t, 1H), 6.98 (d, 1H), 6.48 (d, 1H), 4.89 (br s, 1H), 4.56 (d, 1H), 4.04 (d, 2H), 3.73 (m, 1H), 2.71-2.97 (m, 4H), 2.42 (m, 2H), 2.12 (m, 2H), 1.82-2.02 (m, 5H), 1.44-1.81 (m, 10H), 1.2-1.43 (m, 4H), 0.87 (d, 3H).

Example 2

4-(Tetrahydro-furan-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide

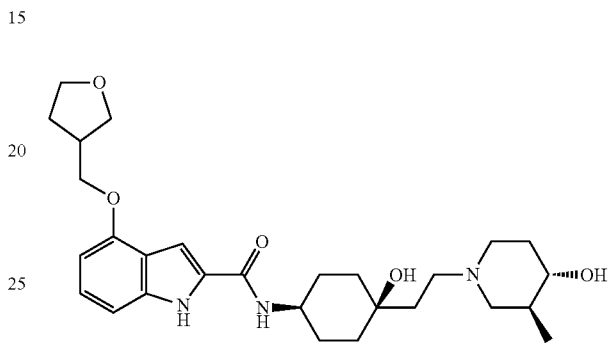

This compound is synthesized analogously to example 1 from 4-(tetrahydro-furan-3-ylmethoxy)-1H-indole-2-carboxylic acid 16b and amine 14.

MS (ESI): 500 [M+H]$^+$, 1H-NMR (DMSO-d$_6$): δ (ppm) 11.42 (s, 1H), 8.21 (d, 1H), 7.22 (s, 1H), 7.02 (t, 1H), 6.97 (d, 1H), 6.47 (d, 1H), 4.82 (s, 1H), 4.51 (d, 1H), 3.93-4.08 (m, 2H), 3.57-3.88 (m, 5H), 2.64-2.96 (m, 4H), 2.4 (m, 2H), 2.05 (m, 1H), 1.87 (m, 1H), 1.67-1.8 (m, 4H), 1.45-1.66 (m, 7H), 1.24-1.42 (m, 4H), 0.87 (d, 3H).

Example 3

4-(Furan-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide

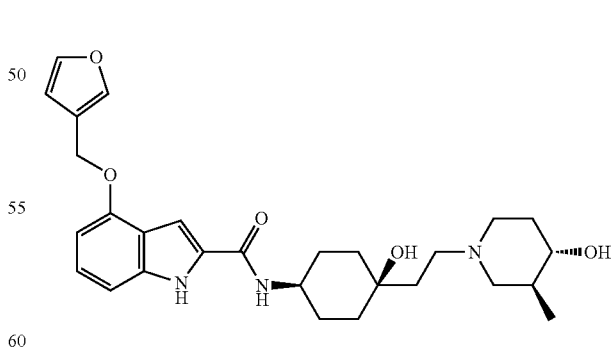

This compound is synthesized analogously to example 1 from 4-(furan-3-ylmethoxy)-1H-indole-2-carboxylic acid 16c and amine 14.

MS (ESI): 496 [M+H]$^+$, 1H-NMR (DMSO-d$_6$): δ (ppm) 11.42 (s, 1H), 8.15 (d, 1H), 7.81 (s, 1H), 7.67 (s, 1H), 7.25 (s, 1H), 7.04 (t, 1H), 6.98 (d, 1H), 6.61 (s, 1H), 6.58 (d, 1H), 5.02

(s, 2H), 4.8 (s, 1H), 4.51 (d, 1H), 3.71 (m, 1H), 2.72-2.94 (m, 3H), 2.4 (m, 2H), 1.86 (m, 1H), 1.44-1.8 (m, 10H), 1.22-1.43 (m, 4H), 0.87 (d, 3H).

Example 4

4-(2-Chloro-thiazol-4-ylmethoxy)-1H-indole-2-carboxylic acid {4-hydroxy-4-[2-((3S,4S)-4-hydroxy-3-methyl-piperidin-1-yl)-ethyl]-cyclohexyl}-amide

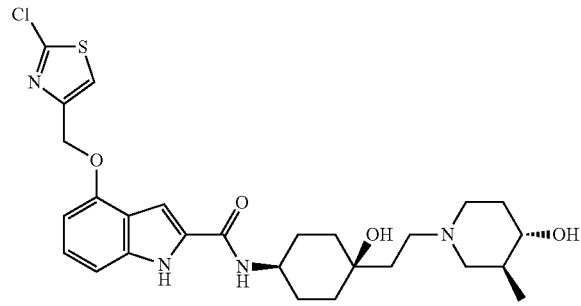 [SMILES: C[C@H]1CN(CC[C@]2(O)CC[C@@H](NC(=O)c3cc4c(OCc5csc(Cl)n5)cccc4[nH]3)CC2)CC[C@@H]1O]

This compound is synthesized analogously to example 1 from 4-(2-chloro-thiazol-4-ylmethoxy)-1H-indole-2-carboxylic acid 16d and amine 14.

MS (ESI): 547 [M+H]$^+$, 1H-NMR (DMSO-d$_6$): δ (ppm) 11.5 (s, 1H), 9.45 (br, 1H), 8.20 (d, 1H), 7.8 (s, 1H), 7.28 (s, 1H), 7.05 (dd, 1H), 7.03 (dd, 1H), 6.63 (d, 1H), 5.2 (s, 1H), 5.05 (br, 1H), 4.37 (br, 1H), 3.75 (m, 1H), 2.72-3.5 (m, 3H), 2.62 (m, 2H), 1.95 (m, 1H), 1.55-1.8 (m, 10H), 1.3-1.45 (m, 4H), 0.95 (d, 3H).

Example 5

4-(6-Methoxy-pyridin-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide

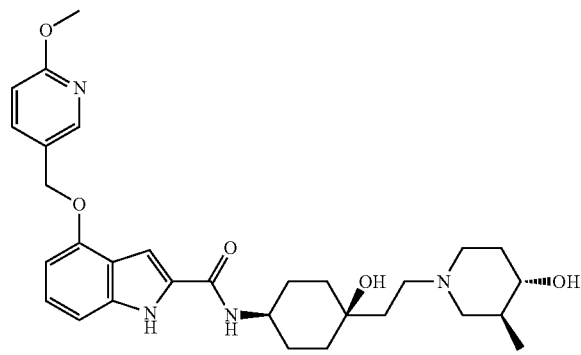 [SMILES: COc1ccc(COc2cccc3[nH]c(C(=O)N[C@H]4CC[C@](O)(CCN5CC[C@H](O)[C@@H](C)C5)CC4)cc23)cn1]

This compound is synthesized analogously to example 1 from 4-(6-methoxy-pyridin-3-ylmethoxy)-1H-indole-2-carboxylic acid 16e and amine 14.

MS (ESI): 537 [M+H]$^+$, 1H-NMR (DMSO-d$_6$): δ (ppm) 11.44 (s, 1H), 8.32 (d, 1H), 8.16 (d, 1H), 7.85 (dd, 1H), 7.26 (d, 1H), 7.07 (t, 1H), 7.0 (d, 1H), 6.87 (d, 1H), 6.62 (d, 1H), 5.13 (s, 2H), 4.81 (s, 1H), 4.52 (d, 1H), 3.87 (s, 3H), 3.71 (m, 1H), 2.75-2.94 (m, 3H), 2.41 (m, 2H), 1.87 (m, 1H), 1.47-1.79 (m, 10H), 1.24-1.42 (m, 4H), 0.88 (d, 3H).

Example 6

4-(4-Oxo-4,5,6,7-tetrahydro-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide

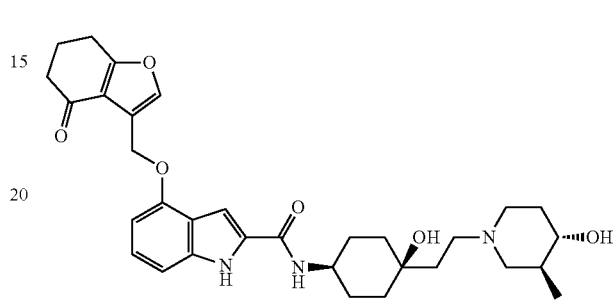

This compound is synthesized analogously to example 1 from 4-(4-oxo-4,5,6,7-tetrahydro-benzofuran-3-ylmethoxy)-1H-indole-2-carboxylic acid 16f and amine 14.

MS (ESI): 564 [M+H]$^+$, 1H-NMR (DMSO-d$_6$): δ (ppm) 11.43 (s, 1H), 8.14 (d, 1H), 7.79 (s, 1H), 7.26 (s, 1H), 7.06 (t, 1H), 7.0 (d, 1H), 6.56 (d, 1H), 5.18 (s, 2H), 4.82 (s, 1H), 4.52 (d, 1H), 3.71 (m, 1H), 2.92 (m, 2H), 2.73-2.88 (m, 3H), 2.35-2.48 (m, 4H), 2.12 (m, 2H), 1.88 (m, 1H), 1.45-1.78 (m, 10H), 1.21-1.43 (m, 4H), 0.88 (d, 3H).

Example 7

4-(6,6-Dimethyl-4-oxo-4,5,6,7-tetrahydro-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide

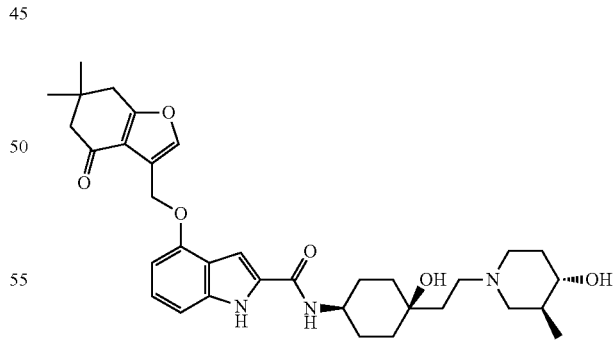

This compound is synthesized analogously to example 1 from 4-(6,6-dimethyl-4-oxo-4,5,6,7-tetrahydro-benzofuran-3-ylmethoxy)-1H-indole-2-carboxylic acid 16 g and amine 14.

MS (ESI): 592 [M+H]$^+$, 1H-NMR (DMSO-d$_6$): δ (ppm) 11.46 (s, 1H), 9.9 (br s, 1H), 8.17 (d, 1H), 7.79 (s, 1H), 7.23 (s, 1H), 7.03 (dd, 1H), 7.0 (dd, 1H), 6.56 (d, 1H), 5.2 (br, 1H), 5.18 (s, 2H), 4.37 (br, 1H), 3.74 (m, 1H), 3.3-3.5 (m, 4H), 3.0-3.2 (m, 3H), 2.82 (s, 2H), 2.36 (s, 2H), 1.9 (m, 2H), 1.5-1.85 (m, 8H), 1.25-1.4 (m, 2H), 1.08 (s, 6H), 0.92 (d, 3H).

Example 8

4-[(S)-1-(2,3-Dihydro-benzofuran-3-yl)methoxy]-1H-indole-2-carboxylic acid {4-hydroxy-4-[2-((3S,4S)-4-hydroxy-3-methyl-piperidin-1-yl)-ethyl]-cyclohexyl}-amide

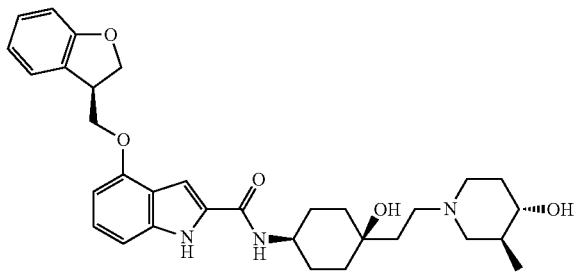 [SMILES: C[C@H]1CN(CC[C@]2(O)CC[C@@H](NC(=O)c3cc4c(OC[C@@H]5COc6ccccc65)cccc4[nH]3)CC2)CC[C@@H]1O]

This compound is synthesized analogously to example 1 from 4-[(S)-1-(2,3-dihydro-benzofuran-3-yl)methoxy]-1H-indole-2-carboxylic acid 16h and amine 14.

MS (ESI): 548 [M+H]$^+$, 1H-NMR (DMSO-d$_6$): δ (ppm) 11.46 (s, 1H), 8.25 (d, 1H), 7.45 (d, 1H), 7.27 (s, 1H), 7.15 (t, 1H), 6.99-7.06 (m, 2H), 6.87 (t, 1H), 6.81 (d, 1H), 6.52 (d, 1H), 4.85 (br s, 1H), 4.73 (t, 1H), 4.53 (d, 1H), 4.48 (dd, 1H), 4.31 (m, 1H), 4.28 (m, 1H), 4.02 (m, 1H), 3.74 (m, 1H), 2.77-2.95 (m, 3H), 2.42 (m, 2H), 1.89 (m, 1H), 1.47-1.81 (m, 10H), 1.27-1.42 (m, 4H), 0.88 (d, 3H).

Example 9

4-((R,S)-6-Methoxy-2,3-dihydro-benzofuran-3-yl-methoxy)-1H-indole-2-carboxylic acid {4-hydroxy-4-[2-((3S,4S)-4-hydroxy-3-methyl-piperidin-1-yl)-ethyl]-cyclohexyl}-amide

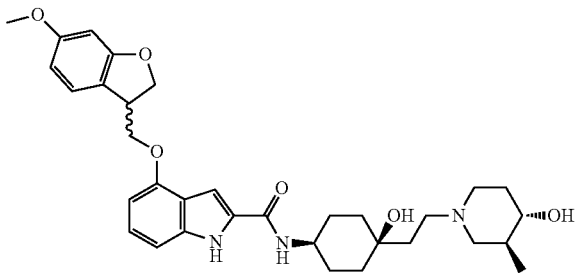 [SMILES: COc1ccc2c(c1)OCC2COc1cccc2[nH]c(C(=O)N[C@H]3CC[C@](O)(CCN4CC[C@H](O)[C@@H](C)C4)CC3)cc12]

This compound is synthesized analogously to example 1 from 4-((R,S)-6-methoxy-2,3-dihydro-benzofuran-3-yl-methoxy)-1H-indole-2-carboxylic acid 16i and amine 14.

MS (ESI): 578 [M+H]$^+$, 1H-NMR (DMSO-d$_6$): δ (ppm) 11.46 (s, 1H), 8.25 (d, 1H), 7.32 (d, 1H), 7.27 (s, 1H), 6.99-7.06 (m, 2H), 6.52 (d, 1H), 6.43 (m, 2H), 4.85 (br s, 1H), 4.74 (t, 1H), 4.54 (br s, 1H), 4.49 (dd, 1H), 4.24 (m, 1H), 4.14 (m, 1H), 3.93 (m, 1H), 3.76 (m, 1H), 3.71 (s, 3H), 2.76-2.98 (m, 3H), 2.44 (m, 2H), 1.9 (m, 1H), 1.46-1.83 (m, 10H), 1.26-1.45 (m, 4H), 0.89 (d, 3H).

Example 10

4-(4-Methoxy-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide

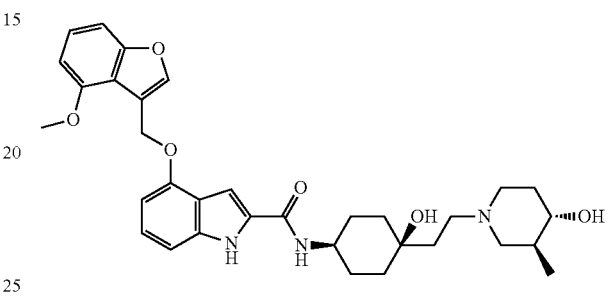

This compound is synthesized analogously to example 1 from 4-(4-methoxy-benzofuran-3-ylmethoxy)-1H-indole-2-carboxylic acid (synthesis described in WO2005077932A2, cmpd 122) and amine 14.

MS (ESI): 576 [M+H]$^+$, 1H-NMR (DMSO-d$_6$): δ (ppm) 11.43 (s, 1H), 8.11 (d, 1H), 8.01 (s, 1H), 7.27 (m, 2H), 7.2 (d, 1H), 7.08 (t, 1H), 7.01 (d, 1H), 6.81 (d, 1H), 6.65 (d, 1H), 5.34 (s, 2H), 4.81 (m, 1H), 4.52 (d, 1H), 3.8 (s, 3H), 3.7 (m, 1H), 2.73-2.95 (m, 3H), 2.4 (m, 2H), 1.87 (m, 1H), 1.46-1.78 (m, 10H), 1.22-1.42 (m, 4H), 0.87 (d, 3H).

Example 11

4-(4,6-Difluoro-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide

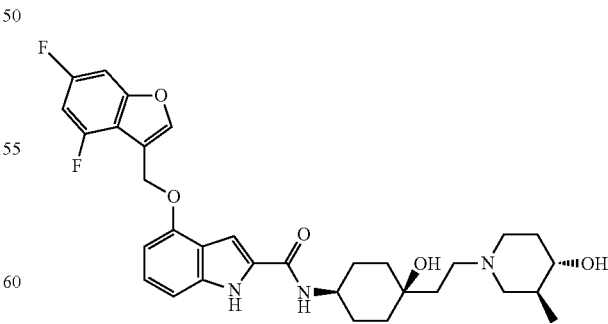

This compound is synthesized analogously to example 1 from 4-(4,6-difluoro-benzofuran-3-ylmethoxy)-1H-indole-2-carboxylic acid (synthesis described in WO2005077932A2, cmpd 115) and amine 14.

MS (ESI): 582 [M+H]$^+$, 1H-NMR (DMSO-d$_6$): δ (ppm) 11.45 (s, 1H), 8.26 (s, 1H), 8.14 (d, 1H), 7.54 (dd, 1H), 7.22 (m, 2H), 7.08 (t, 1H), 7.02 (d, 1H), 6.68 (d, 1H), 5.3 (s, 2H), 4.8 (m, 1H), 4.51 (d, 1H), 3.7 (m, 1H), 2.72-2.95 (m, 3H), 2.4 (m, 2H), 1.87 (m, 1H), 1.45-1.79 (m, 10H), 1.22-1.43 (m, 4H), 0.87 (d, 3H).

Example 12

4-(5-Chloro-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide

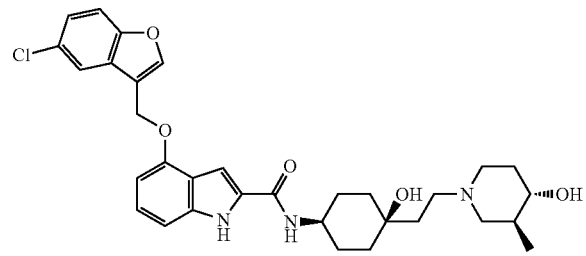 [SMILES: C[C@H]1CN(CC[C@]2(O)CC[C@@H](NC(=O)c3cc4c(OCc5coc6ccc(Cl)cc56)cccc4[nH]3)CC2)CC[C@@H]1O]

This compound is synthesized analogously to example 1 from 4-(5-chloro-benzofuran-3-ylmethoxy)-1H-indole-2-carboxylic acid (synthesis described in WO2005077932A2, cmpd 113) and amine 14.

MS (ESI): 581 [M+H]$^+$, 1H-NMR (DMSO-d$_6$): δ (ppm) 11.49 (s, 1H), 8.27 (s, 1H), 8.16 (d, 1H), 7.81 (d, 1H), 7.69 (d, 1H), 7.41 (d, 1H), 7.39 (s, 1H), 7.26 (s, 1H), 7.11 (t, 1H), 7.05 (d, 1H), 6.72 (d, 1H), 5.37 (s, 2H), 4.53 (d, 1H), 3.72 (m, 1H), 2.91 (m, 1H), 2.82 (m, 2H), 2.42 (m, 2H), 1.89 (m, 1H), 1.46-1.8 (m, 10H), 1.23-1.43 (m, 4H), 0.88 (d, 3H).

Example 13

4-(6-Methoxy-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide

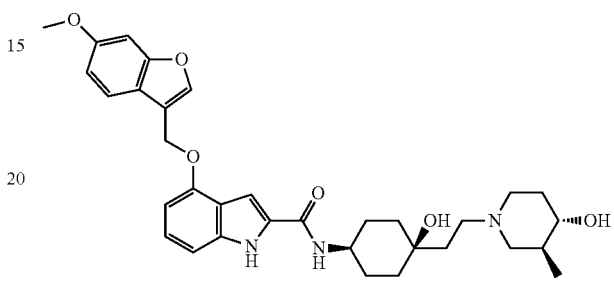

This compound is synthesized analogously to example 1 from 4-(6-methoxy-benzofuran-3-ylmethoxy)-1H-indole-2-carboxylic acid (synthesis described in WO2005077932A2, cmpd 120) and amine 14.

MS (ESI): 576 [M+H]$^+$, 1H-NMR (DMSO-d$_6$): δ (ppm) 11.44 (s, 1H), 8.14 (d, 1H), 8.03 (s, 1H), 7.57 (d, 1H), 7.22 (m, 2H), 7.08 (t, 1H), 7.01 (d, 1H), 6.93 (dd, 1H), 6.69 (d, 1H), 5.31 (s, 2H), 4.8 (br s, 1H), 4.51 (d, 1H), 3.81 (s, 3H), 3.7 (m, 1H), 2.73-2.96 (m, 3H), 2.4 (m, 2H), 1.86 (m, 1H), 1.45-1.79 (m, 10H), 1.24-1.42 (m, 4H), 0.87 (d, 3H).

Example 14

4-(6-Ethoxy-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide

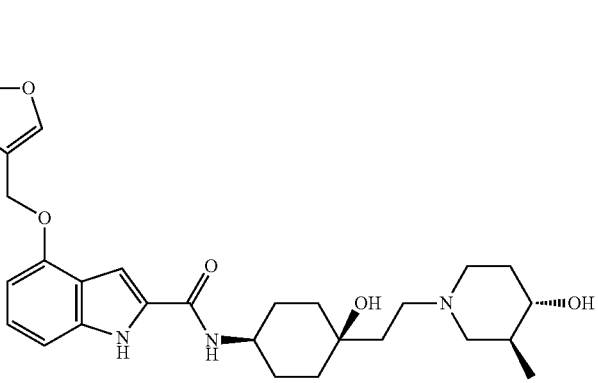

This compound is synthesized analogously to example 1 from 4-(6-ethoxy-benzofuran-3-ylmethoxy)-1H-indole-2-carboxylic acid 30a and amine 14.

MS (ESI): 590 [M+H]$^+$, 1H-NMR (DMSO-d$_6$): δ (ppm) 11.45 (s, 1H), 9.3 (br, 1H), 8.15 (d, 1H), 8.03 (s, 1H), 7.55 (d, 1H), 7.23 (s, 1H), 7.19 (s, 1H), 7.08 (dd, 1H), 7.02 (d, 1H), 6.92 (m, 1H), 6.7 (d, 1H), 5.3 (s, 2H), 4.06 (q, 2H), 3.7-3.9 (m, 3H), 3.0-3.25 (m, 3H), 2.94 (m, 2H), 2.61 (m, 2H), 1.5-1.8 (m, 12H), 1.35 (t, 3H), 0.94 (d, 3H).

Example 15

4-(6-Cyclopropylmethoxy-benzofuran-3-yl-methoxy)-1H-indole-2-carboxylic acid {4-hydroxy-4-[2-((3S,4S)-4-hydroxy-3-methyl-piperidin-1-yl)-ethyl]-cyclohexyl}-amide

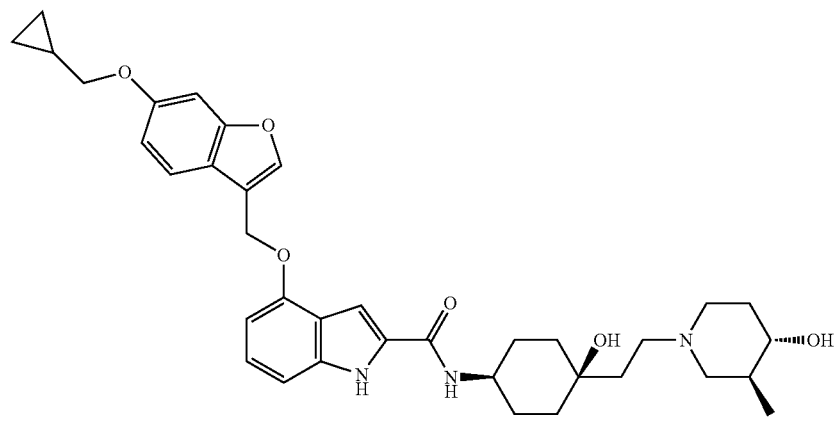 [SMILES: C[C@H]1CN(CC[C@]2(O)CC[C@@H](NC(=O)c3cc4c(OCc5coc6cc(OCC7CC7)ccc56)cccc4[nH]3)CC2)CC[C@@H]1O]

This compound is synthesized analogously to example 1 from 4-(6-cyclopropylmethoxy-benzofuran-3-ylmethoxy)-1H-indole-2-carboxylic acid 30b and amine 14.

MS (ESI): 616 [M+H]$^+$, 1H-NMR (DMSO-d$_6$): δ (ppm) 11.45 (s, 1H), 9.7 (br, 1H), 8.17 (d, 1H), 8.02 (s, 1H), 7.55 (d, 1H), 7.22 (d, 1H), 7.18 (d, 1H), 7.08 (dd, 1H), 7.0 (d, 1H), 6.9 (dd, 1H), 6.68 (d, 1H), 5.7 (s, 2H), 5.0 (br, 1H), 4.38 (br, 1H), 3.85 (d, 2H), 3.65-3.9 (m, 2H), 2.5-3.5 (m, 6H), 1.3-2.0 (m, 13H), 0.92 (d, 3H), 0.55-0.6 (m, 2H), 0.3-0.38 (m, 2H).

Example 16

4-[6-(2-Ethoxy-ethoxy)-benzofuran-3-ylmethoxy]-1H-indole-2-carboxylic acid {4-hydroxy-4-[2-((3S,4S)-4-hydroxy-3-methyl-piperidin-1-yl)-ethyl]-cyclohexyl}-amide

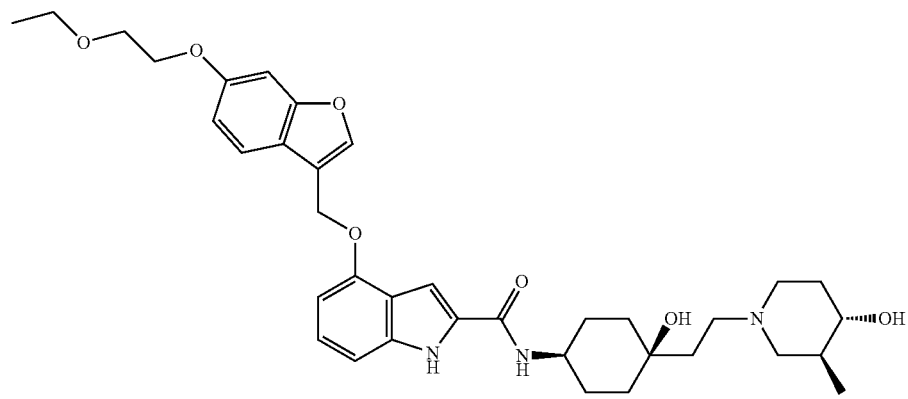 [SMILES: CCOCCOc1ccc2c(COc3cccc4[nH]c(C(=O)N[C@H]5CC[C@](O)(CCN6CC[C@H](O)[C@@H](C)C6)CC5)cc34)coc2c1]

This compound is synthesized analogously to example 1 from 4-[6-(2-ethoxy-ethoxy)-benzofuran-3-ylmethoxy]-1H-indole-2-carboxylic acid 30c and amine 14.

MS (ESI): 634 [M+H]⁺, 1H-NMR (DMSO-d₆): δ (ppm) 11.44 (s, 1H), 9.7 (br, 1H), 8.15 (d, 1H), 8.02 (s, 1H), 7.56 (d, 1H), 7.22 (d, 1H), 7.2 (m, 1H), 7.08 (dd, 1H), 7.0 (d, 1H), 6.92 (dd, 1H), 6.68 (d, 1H), 5.3 (s, 2H), 5.0 (br, 1H), 4.38 (br, 1H), 4.13 (t, 2H), 3.7 (t, 2H), 3.68-3.75 (m, 1H), 3.5 (q, 2H), 2.7-2.9 (m, 3H), 2.39 (m, 2H), 1.2-2.0 (m, 14H), 1.13 (t, 3H), 0.9 (d, 3H).

1H), 7.22 (m, 1H), 7.21 (m, 1H), 7.08 (dd, 1H), 7.0 (d, 1H), 6.9 (dd, 1H), 6.68 (d, 1H), 5.3 (s, 2H), 5.1 (br, 1H), 4.65 (m, 1H), 4.4 (br, 1H), 4.08 (m, 1H), 3.7 (m, 2H), 3.65-3.9 (m, 1H), 3.42-3.55 (m, 2H), 3.25-3.35 (m, 5H), 3.18 (m, 2H), 1.2-2.0 (m, 12H), 1.23 (d, 3H), 0.9 (d, 3H).

Example 17

4-[6-((RS)-2-Methoxy-1-methyl-ethoxy)-benzofuran-3-ylmethoxy]-1H-indole-2-carboxylic acid {4-hydroxy-4-[2-((3S,4S)-4-hydroxy-3-methyl-piperidin-1-yl)-ethyl]-cyclohexyl}-amide

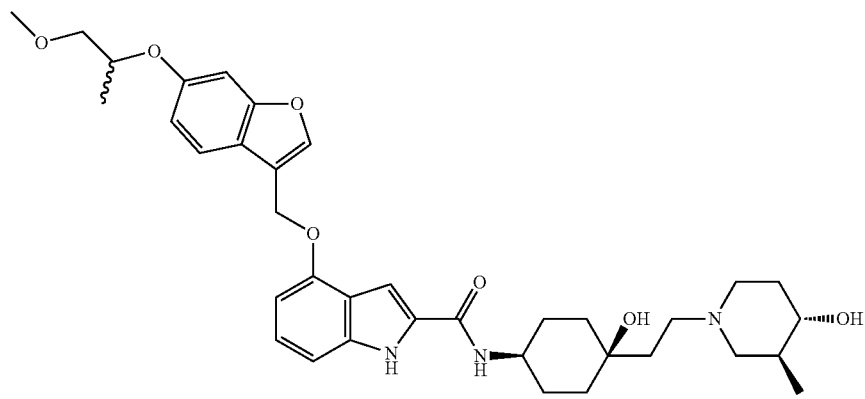 [SMILES: COCC(C)Oc1ccc2c(COc3cccc4[nH]c(C(=O)N[C@H]5CC[C@](O)(CCN6CC[C@H](O)[C@@H](C)C6)CC5)cc34)coc2c1]

This compound is synthesized analogously to example 1 from 4-[6-((RS)-2-Methoxy-1-methyl-ethoxy)-benzofuran-3-ylmethoxy]-1H-indole-2-carboxylic acid 30d and amine 14.

MS (ESI): 634.4 [M+H]⁺, 1H-NMR (DMSO-d₆): δ (ppm) 11.45 (s, 1H), 9.53 (br, 1H), 8.15 (d, 1H), 8.03 (s, 1H), 7.55 (d,

Example 18

4-[6-(2-Isopropoxy-ethoxy)-benzofuran-3-yl-methoxy]-1H-indole-2-carboxylic acid {4-hydroxy-4-[2-((3S,4S)-4-hydroxy-3-methyl-piperidin-1-yl)-ethyl]-cyclohexyl}-amide

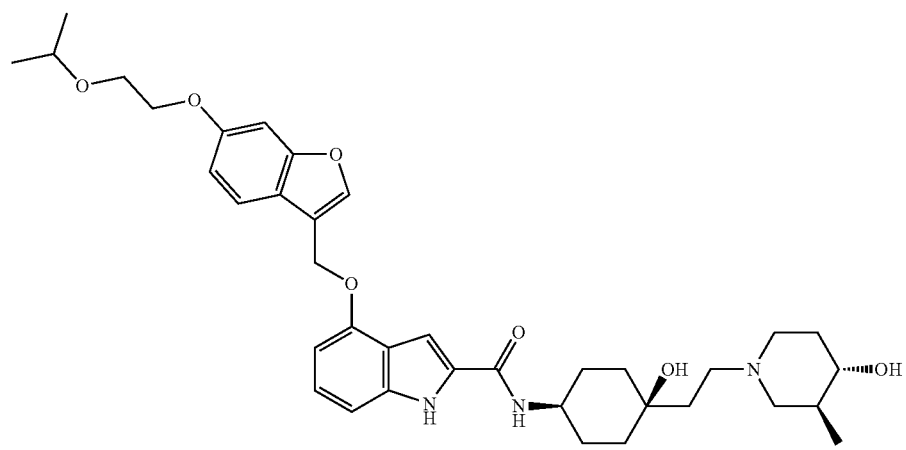 [SMILES: CC(C)OCCOc1ccc2c(COc3cccc4[nH]c(C(=O)N[C@H]5CC[C@](O)(CCN6CC[C@H](O)[C@@H](C)C6)CC5)cc34)coc2c1]

This compound is synthesized analogously to example 1 from 4-[6-(2-Isopropoxy-ethoxy)-benzofuran-3-yl-methoxy]-1H-indole-2-carboxylic acid 30e and amine 14.

MS (ESI): 648.4 [M+H]$^+$, 1H-NMR (DMSO-d$_6$): δ (ppm) 11.46 (s, 1H), 9.9 (br, 1H), 8.15 (d, 1H), 8.02 (s, 1H), 7.55 (d, 1H), 7.22 (s, 1H), 7.22 (s, 1H), 7.07 (dd, 1H), 7.01 (d, 1H), 6.92 (dd, 1H), 6.69 (d, 1H), 5.3 (s, 2H), 5.02 (br d, 1H), 4.35 (s, 1H), 4.1 (t, 2H), 3.7 (m, 3H), 3.62 (m, 1H), 3.3-3.45 (m, 2H), 3.15 (m, 1H), 3.05 (m, 2H), 2.9 (m, 1H), 2.58 (m, 1H), 1.25-2.0 (m, 12H), 1.11 (d, 6H), 0.92 (d, 3H).

Example 19

4-[6-(3-Methoxy-propoxy)-benzofuran-3-yl-methoxy]-1H-indole-2-carboxylic acid {4-hydroxy-4-[2-((3S,4S)-4-hydroxy-3-methyl-piperidin-1-yl)-ethyl]-cyclohexyl}-amide

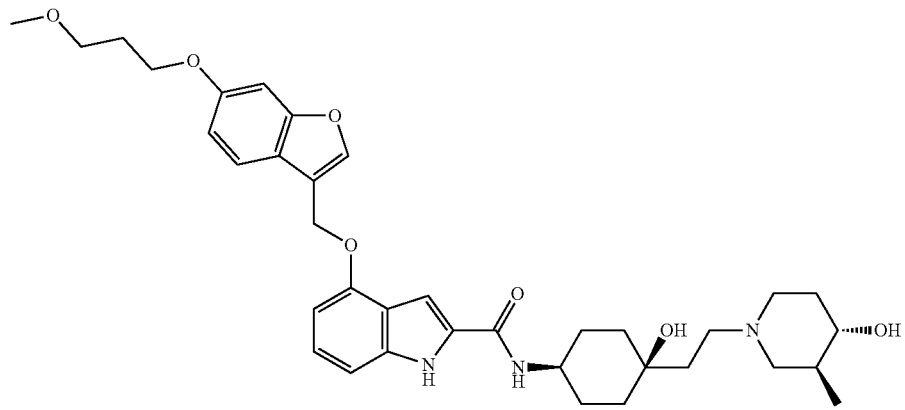 [SMILES: COCCCOc1ccc2c(COc3cccc4[nH]c(C(=O)N[C@H]5CC[C@](O)(CCN6CC[C@H](O)[C@@H](C)C6)CC5)cc34)coc2c1]

This compound is synthesized analogously to example 1 from 4-[6-(3-methoxy-propoxy)-benzofuran-3-ylmethoxy]-1H-indole-2-carboxylic acid 30f and amine 14.

MS (ESI): 634 [M+H]$^+$, 1H-NMR (DMSO-d$_6$): δ (ppm) 11.46 (s, 1H), 9.92 (br, 1H), 8.15 (d, 1H), 8.02 (s, 1H), 7.55 (d, 1H), 7.22 (s, 1H), 7.19 (s, 1H), 7.05 (dd, 1H), 7.01 (d, 1H), 6.91 (d, 1H), 6.68 (d, 1H), 5.3 (s, 2H), 4.2 (br, 2H), 4.05 (t, 2H), 3.72 (m, 1H), 3.47 (t, 2H), 3.3-3.45 (m, 2H), 3.24 (s, 3H), 3.15 (m, 2H), 3.06 (m, 2H), 2.9 (m, 1H), 2.6 (m, 1H), 1.25-2.0 (m, 13H), 0.92 (d, 3H).

Example 20

4-[6-(3-Ethoxy-propoxy)-benzofuran-3-ylmethoxy]-1H-indole-2-carboxylic acid {4-hydroxy-4-[2-((3S,4S)-4-hydroxy-3-methyl-piperidin-1-yl)-ethyl]-cyclohexyl}-amide

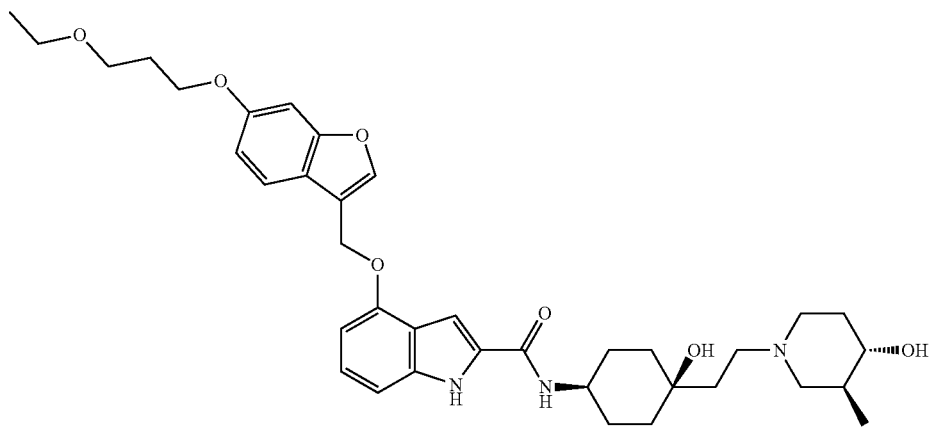 [SMILES: CCOCCCOc1ccc2c(COc3cccc4[nH]c(C(=O)N[C@H]5CC[C@](O)(CCN6CC[C@H](O)[C@@H](C)C6)CC5)cc34)coc2c1]

This compound is synthesized analogously to example 1 from 4-[6-(3-ethoxy-propoxy)-benzofuran-3-ylmethoxy]-1H-indole-2-carboxylic acid 30g and amine 14.

MS (ESI): 648.5 [M+H]$^+$, 1H-NMR (DMSO-d$_6$): δ (ppm) 11.47 (s, 1H), 10.1 (br, 1H), 8.15 (d, 1H), 8.02 (s, 1H), 7.55 (d, 1H), 7.22 (s, 1H), 7.19 (s, 1H), 7.07 (dd, 1H), 7.01 (d, 1H), 6.91 (d, 1H), 6.68 (d, 1H), 5.29 (s, 2H), 5.0-5.5 (br, 2H), 4.06 (t, 2H), 3.72 (m, 1H), 3.51 (t, 2H), 3.35-3.45 (m, 3H), 3.31 (m, 1H), 3.15 (m, 1H), 3.06 (m, 2H), 2.91 (m, 1H), 2.57 (m, 1H), 1.25-2.0 (m, 14H), 1.10 (t, 3H), 0.92 (d, 3H).

Example 21

4-{6-[(S)-(Tetrahydro-furan-3-yl)oxy]-benzofuran-3-ylmethoxy}-1H-indole-2-carboxylic acid {4-hydroxy-4-[2-((3S,4S)-4-hydroxy-3-methyl-piperidin-1-yl)-ethyl]-cyclohexyl}-amideamide

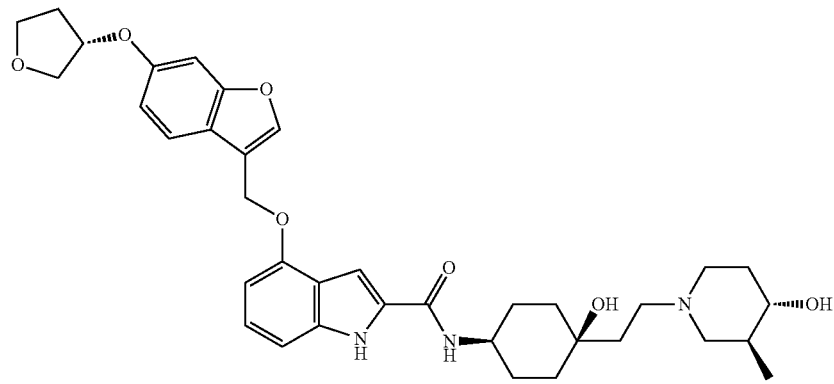 [SMILES: C[C@H]1CN(CC[C@]2(O)CC[C@@H](NC(=O)c3cc4c(OCc5coc6cc(O[C@H]7CCOC7)ccc56)cccc4[nH]3)CC2)CC[C@@H]1O]

This compound is synthesized analogously to example 1 from 4-{6-[(S)-(tetrahydro-furan-3-yl)oxy]-benzofuran-3-ylmethoxy}-1H-indole-2-carboxylic acid 30h and amine 14.

MS (ESI): 632 [M+H]$^+$, 1H-NMR (DMSO-d$_6$): δ (ppm) 11.45 (s, 1H), 9.8 (br, 1H), 8.15 (d, 1H), 8.02 (s, 1H), 7.55 (d, 1H), 7.22 (s, 1H), 7.19 (s, 1H), 7.07 (dd, 1H), 7.01 (d, 1H), 6.90 (d, 1H), 6.69 (d, 1H), 5.29 (s, 2H), 5.07 (m, 1H), 5.0 (br, 1H), 4.4 (br, 1H), 3.6-3.95 (m, 5H), 2.6-2.9 (m, 3H), 2.38 (t, 2H), 2.22 (m, 2H), 1.2-2.0 (m, 14H), 0.86 (d, 3H).

Example 22

4-(6-Fluoro-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide

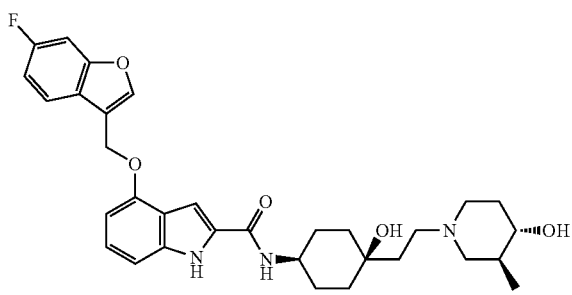 [SMILES: C[C@H]1CN(CC[C@]2(O)CC[C@@H](NC(=O)c3cc4c(OCc5coc6cc(F)ccc56)cccc4[nH]3)CC2)CC[C@@H]1O]

This compound is synthesized analogously to example 1 from 4-(6-fluoro-benzofuran-3-ylmethoxy)-1H-indole-2-carboxylic acid (synthesis described in WO2005077932A2, cmpd 106) and amine 14.

MS (ESI): 564 [M+H]$^+$, 1H-NMR (DMSO-d$_6$): δ (ppm) 11.44 (s, 1H), 8.19 (s, 1H), 8.13 (d, 1H), 7.72 (dd, 1H), 7.58 (dd, 1H), 7.23 (s, 1H), 7.19 (m, 1H), 7.08 (t, 1H), 7.01 (d, 1H), 6.7 (d, 1H), 5.35 (s, 2H), 4.79 (br s, 1H), 4.51 (d, 1H), 3.7 (m, 1H), 2.73-2.95 (m, 3H), 2.4 (m, 2H), 1.87 (m, 1H), 1.45-1.79 (m, 10H), 1.2-1.44 (m, 4H), 0.88 (d, 3H).

Example 23

4-(7-Methoxy-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide

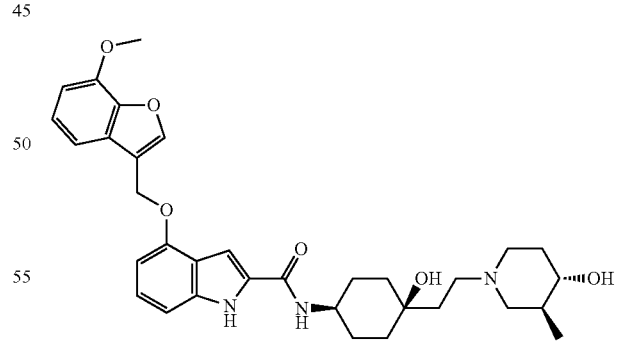

This compound is synthesized analogously to example 1 from 4-(7-methoxy-benzofuran-3-ylmethoxy)-1H-indole-2-carboxylic acid (synthesis described in WO2005077932A2, cmpd 119) and amine 14.

MS (ESI): 576 [M+H]$^+$, 1H-NMR (DMSO-d$_6$): δ (ppm) 11.46 (s, 1H), 8.16 (d, 1H), 8.13 (s, 1H), 7.27 (m, 1H), 7.17-7.25 (m, 2H), 7.05-7.1 (m, 1H), 7.02 (m, 1H), 6.97 (m, 1H), 6.71 (m, 1H), 5.33 (s, 2H), 4.99 (br, 1H), 4.3 (br, 1H), 3.94 (s, 3H), 3.71 (m, 1H), 2.8-3.4 (m, 7H), 1.91 (m, 2H), 1.5-1.8 (m, 7H), 1.34 (m, 4H), 0.92 (d, 3H).

Example 24

4-[2-(2-Methoxy-phenyl)-ethoxy]-1H-indole-2-carboxylic acid {4-hydroxy-4-[2-((3S,4S)-4-hydroxy-3-methyl-piperidin-1-yl)-ethyl]-cyclohexyl}-amide

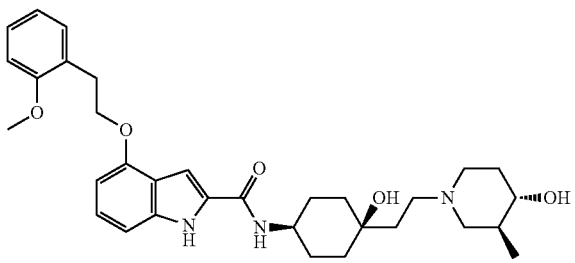 [SMILES: COc1ccccc1CCOc1cccc2[nH]c(C(=O)N[C@H]3CC[C@](O)(CCN4CC[C@H](O)[C@@H](C)C4)CC3)cc12]

This compound is synthesized analogously to example 1 from 4-[2-(2-methoxy-phenyl)-ethoxy]-1H-indole-2-carboxylic acid 16j and amine 14.

MS (ESI): 550 [M+H]$^+$, 1H-NMR (DMSO-d$_6$): δ (ppm) 11.44 (s, 1H), 8.22 (d, 1H), 7.79 (d, 0.5H), 7.54 (d, 0.5H), 7.2-7.32 (m, 4H), 6.96-7.05 (m, 3H), 6.9 (t, 1H), 6.5 (d, 1H), 4.73 (br s, 1H), 4.23 (t, 2H), 3.82 (s, 3H), 3.73 (m, 1H), 3.1 (t, 2H), 2.93-3.06 (br m, 3H), 2.6-2.75 (br m, 2H), 1.41-1.87 (m, 11H), 1.14-1.4 (m, 3H), 0.91 (d, 3H).

Example 25

4-[2-(3-Methoxy-phenyl)-ethoxy]-1H-indole-2-carboxylic acid {4-hydroxy-4-[2-((3S,4S)-4-hydroxy-3-methyl-piperidin-1-yl)-ethyl]-cyclohexyl}-amide

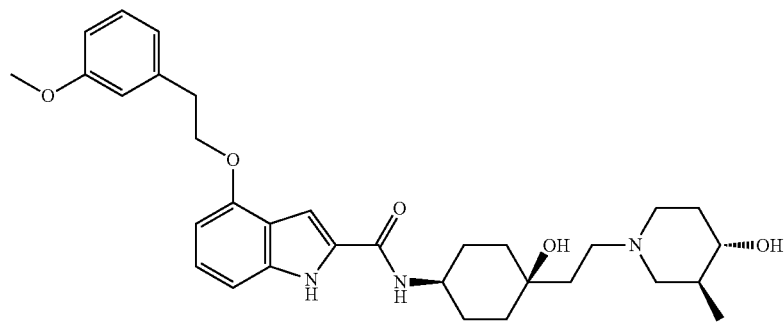 [SMILES: COc1cccc(CCOc2cccc3[nH]c(C(=O)N[C@H]4CC[C@](O)(CCN5CC[C@H](O)[C@@H](C)C5)CC4)cc23)c1]

This compound is synthesized analogously to example 1 from 4-[2-(3-methoxy-phenyl)-ethoxy]-1H-indole-2-carboxylic acid 16k and amine 14.

MS (ESI): 550 [M+H]$^+$, 1H-NMR (DMSO-d$_6$): δ (ppm) 11.41 (s, 1H), 8.2 (d, 1H), 7.24 (s, 1H), 7.22 (t, 1H), 6.93-7.05 (m, 4H), 6.79 (m, 1H), 6.49 (d, 1H), 4.83 (br s, 1H), 4.52 (d, 1H), 4.29 (t, 2H), 3.74 (s, 3H, and overlapping m, 1H), 3.09 (t, 2H), 2.75-2.96 (m, 3H), 2.42 (t, 2H), 1.88 (m, 1H), 1.47-1.81 (m, 10H), 1.21-1.45 (m, 4H), 0.88 (d, 3H).

Example 26

4-[2-(4-Methoxy-phenyl)-ethoxy]-1H-indole-2-carboxylic acid {4-hydroxy-4-[2-((3S,4S)-4-hydroxy-3-methyl-piperidin-1-yl)-ethyl]-cyclohexyl}-amide

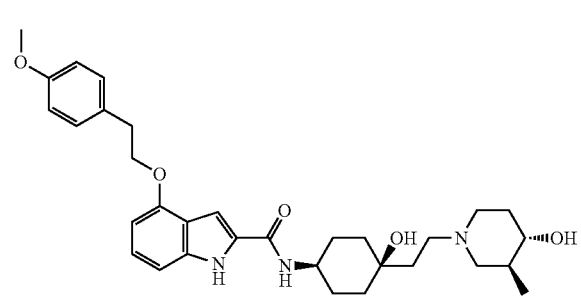 [SMILES: COc1ccc(CCOc2cccc3[nH]c(C(=O)N[C@H]4CC[C@](O)(CCN5CC[C@H](O)[C@@H](C)C5)CC4)cc23)cc1]

This compound is synthesized analogously to example 1 from 4-[2-(4-methoxy-phenyl)-ethoxy]-1H-indole-2-carboxylic acid 16l and amine 14.

MS (ESI): 550 [M+H]$^+$, 1H-NMR (DMSO-d$_6$): δ (ppm) 11.42 (s, 1H), 8.21 (d, 1H), 7.28 (d, 2H), 7.24 (s, 1H), 7.02 (t, 1H), 6.97 (d, 1H), 6.87 (d, 2H), 6.48 (d, 1H), 4.84 (br s, 1H), 4.52 (d, 1H), 4.23 (t, 2H), 3.72 (s, 3H, and overlapping m, 1H), 3.05 (t, 2H), 2.76-2.96 (m, 3H), 2.42 (t, 2H), 1.89 (m, 1H), 1.47-1.82 (m, 10H), 1.25-1.45 (m, 4H), 0.88 (d, 3H).

Example 27

4-[2-(2-Methoxy-pyridin-3-yl)-ethoxy]-1H-indole-2-carboxylic acid {4-hydroxy-4-[2-((3S,4S)-4-hydroxy-3-methyl-piperidin-1-yl)-ethyl]-cyclohexyl}-amide

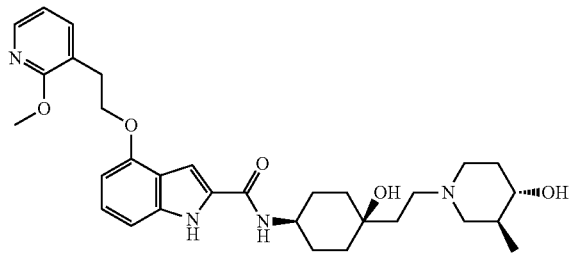 [SMILES: COc1ncccc1CCOc1cccc2[nH]c(C(=O)N[C@H]3CC[C@](O)(CCN4CC[C@H](O)[C@@H](C)C4)CC3)cc12]

This compound is synthesized analogously to example 1 from 4-[2-(2-methoxy-pyridin-3-yl)-ethoxy]-1H-indole-2-carboxylic acid 16m and amine 14.

MS (ESI): 551 [M+H]$^+$, 1H-NMR (DMSO-d$_6$): δ (ppm) 11.42 (s, 1H), 8.18 (d, 1H), 8.05 (m, 1H), 7.68 (m, 1H), 7.21 (s, 1H), 7.03 (t, 1H), 6.94-6.98 (m, 2H), 6.51 (d, 1H), 4.84 (br s, 1H), 4.53 (d, 1H), 4.28 (t, 2H), 3.9 (s, 3H), 3.72 (m, 1H), 3.08 (t, 2H), 2.75-2.95 (m, 3H), 2.42 (t, 2H), 1.88 (m, 1H), 1.45-1.81 (m, 10H), 1.25-1.44 (m, 4H), 0.88 (d, 3H).

Example 28

4-[2-(6-Methoxy-pyridin-3-yl)-ethoxy]-1H-indole-2-carboxylic acid {4-hydroxy-4-[2-((3S,4S)-4-hydroxy-3-methyl-piperidin-1-yl)-ethyl]-cyclohexyl}-amide

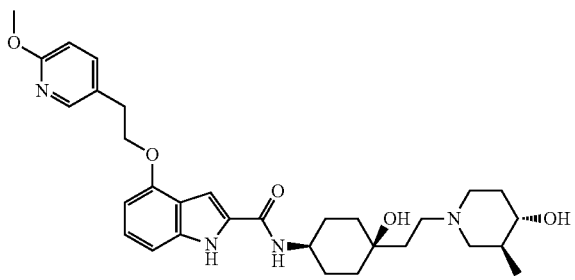 [SMILES: COc1ccc(CCOc2cccc3[nH]c(C(=O)N[C@H]4CC[C@](O)(CCN5CC[C@H](O)[C@@H](C)C5)CC4)cc23)cn1]

This compound is synthesized analogously to example 1 from 4-[2-(6-methoxy-pyridin-3-yl)-ethoxy]-1H-indole-2-carboxylic acid 16n and amine 14.

MS (ESI): 551 [M+H]$^+$, 1H-NMR (DMSO-d$_6$): δ (ppm) 11.43 (s, 1H), 8.21 (d, 1H), 8.15 (d, 1H), 7.73 (dd, 1H), 7.23 (s, 1H), 7.02 (t, 1H), 6.97 (d, 1H), 6.77 (d, 1H), 6.48 (d, 1H), 4.84 (br s, 1H), 4.53 (d, 1H), 4.25 (t, 2H), 3.82 (s, 3H), 3.73 (m, 1H), 3.06 (t, 2H), 2.77-2.94 (m, 3H), 2.42 (t, 2H), 1.88 (m, 1H), 1.46-1.81 (m, 10H), 1.24-1.43 (m, 4H), 0.88 (d, 3H).

Example 29

4-[2-(6-Methoxy-benzofuran-3-yl)-ethoxy]-1H-indole-2-carboxylic acid {4-hydroxy-4-[2-((3S,4S)-4-hydroxy-3-methyl-piperidin-1-yl)-ethyl]-cyclohexyl}-amide

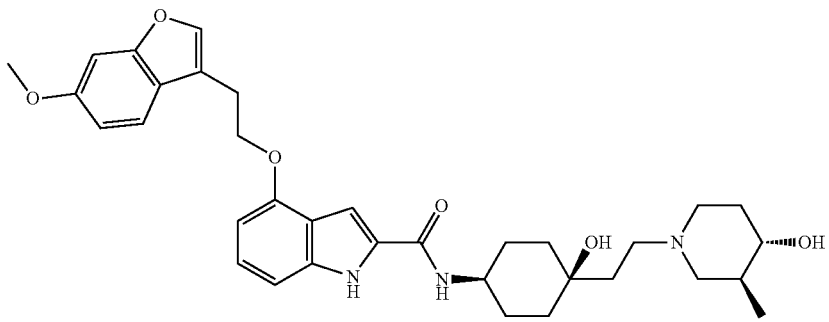 [SMILES: COc1ccc2c(CCOc3cccc4[nH]c(C(=O)N[C@H]5CC[C@](O)(CCN6CC[C@H](O)[C@@H](C)C6)CC5)cc34)coc2c1]

This compound is synthesized analogously to example 1 from 4-[2-(6-methoxy-benzofuran-3-yl)-ethoxy]-1H-indole-2-carboxylic acid 16o and amine 14.

MS (ESI): 590 [M+H]$^+$, 1H-NMR (DMSO-d$_6$): δ (ppm) 11.42 (s, 1H), 8.19 (d, 1H), 7.76 (s, 1H), 7.61 (d, 1H), 7.25 (s, 1H), 7.14 (d, 1H), 7.02 (t, 1H), 6.97 (d, 1H), 6.87 (dd, 1H), 6.5 (d, 1H), 4.82 (br s, 1H), 4.52 (d, 1H), 4.34 (t, 2H), 3.78 (s, 3H), 3.71 (m, 1H), 3.15 (t, 2H), 2.74-2.93 (m, 3H), 2.41 (t, 2H), 1.87 (m, 1H), 1.46-1.8 (m, 10H), 1.25-1.42 (m, 4H), 0.87 (d, 3H).

The compounds of formula I in free form or in pharmaceutically acceptable salt form exhibit valuable pharmacological properties, e.g. as CCR2 and CCR5 antagonists as indicated in in vitro tests as described below.

a) CCR2 Membrane Binding Assay

The SPA (Scintillation Proximity Assay) technology is used to show that the test compounds prevent MCP-1 from binding to cell membranes expressing the CCR2 receptor. Transfected CHO-dukX cells stably expressing the hCCR2b gene are grown in MEM alpha medium to a confluency of between 70 and 80%. After discarding the medium, 30 ml ice-cold physiological buffer solution containing 1 mM EDTA are added and the cells removed from the plate using a scraper. The cell suspension is centrifuged at 800 g for 10' at 4° C. and the cell pellet resuspended in buffer. Cell lysis is done using a Polytron PTI300D instrument at 28 000 RPM for 2 times 30 seconds on ice. Membranes are collected by centrifugation at 42 000 g for 20 minutes at 4° C. and subjected to a second round of lysis (Polytron, 28 000 RPM, 2×30 seconds on ice). Following centrifugation at 42 000 g for 20 minutes at 4° C. the membranes are resuspended in buffer at a protein concentration of 2 mg/ml and stored at −80° C. Ten millimolar stock solutions of test compounds in 100% DMSO are prepared. Test compounds are further diluted in buffer to yield the four-fold concentrated solutions for the tests that assayed a range of $10^{-10}$ to $10^{-5}$ M. The SPA assay is performed in a final volume of 200 µl per well in 96 well plates. The components are added per well in the following order:

50 µl Buffer (+/−test compound)
50 µl Wheat germ agglutinin-SPA beads (1.25 mg/well) in buffer
50 µl CCR2B membrane suspension diluted with buffer to 0.04 mg/ml (2 µg/well), alternatively 50,000 cells per well
50 µl [$^{125}$I] MCP-1 in buffer (60 pM final concentration, 2.5 µCi/plate)

After addition of all components the plate is sealed and incubated for 90 minutes at room temperature with constant shaking. Following incubation the plate is centrifuged at 1000 RPM in a Sorvall RC3B centrifuge for 4 minutes at room temperature and counted for 3 minutes per well in a TOP COUNT instrument (Packard). The quench-corrected counts are used for the analysis of radioligand binding.

Compounds of formula I have an $IC_{50}$ between 0.002 and 10 µM:

In a similar manner, binding assays for the rat, mouse and rhesus monkey CCR2 receptors have been established. Due to the species specificity of the CCR2 antagonists, the compounds of formula I have an $IC_{50}$ between 0.015 and 10 µM on mouse CCR2 and between 0.020 and 10 µM on rat CCR2.

b) CCR2 Functional Assay—Chemotaxis

A micro-transwell chemotaxis assay with human peripheral blood monocytes was used to profile CCR2 antagonists. Human peripheral blood mononuclear cells (PBMCs) were isolated from donor blood buffy coats by density centrifugation on a Ficoll-Paque gradient. PBMCs collected from the interface were washed frozen at −80° C. until use. Chemotaxis assays were performed with MultiScreen-MIC 96-well plates with 5-µm pore polycarbonate filters. Cell suspensions and MCP-1 (1 nM) were made in RPMI1640 with glutamax supplemented with 1% nonessential amino acids, sodium pyruvate, penicillin/streptomycin, 50 µM β-mercaptoethanol and 1% human albumin. Frozen PBMCs were thawed, washed and resuspended at $2×10^6$/ml. For assessing the inhibitory effect of the compounds on CCR2-mediated chemotaxis, cells, MCP-1 and compounds were prepared as 2-fold concentrated solutions, mixed and placed into the filter plate and receiver plate. It is important to note that the compounds were pre-diluted in DMSO at a 2000-fold molar excess so that the final DMSO concentration was 0.05% in the chemotaxis assay (this DMSO concentration was shown to have no effect on chemotaxis). To ensure an uniform concentration, the compounds were added to the upper compartment (cells) as well as to the lower compartment (chemokine). After migration for 3 hr at 37° C. in an incubator, the filter plate was carefully removed from the receiver plate and discarded. The migrated cells in the receiver plate were resuspended and transferred into round-bottom 96-well plate, centrifuged and resuspended in 100 µl PBS containing 2% FCS and 0.1% $NaN_3$. The input cells (100 µl) were similarly processed. For the calculation of the specific migration, a fixed number of beads (10000) in 20 µl buffer was added and the suspension was analyzed by flow cytometry using a FACScalibur equipped with an AutoSampler MAS-1 and CellQuest software with established settings for PBMCs and beads. Monocytes were identified based on their forward scatter (FSC) and side scatter (SSC) pattern. Chemotaxis is expressed as percent of input monocytes using the following formula: ((% monocytes/% beads)/(% input monocytes/% input beads))*100.

c) CCR5 Functional Assay—Chemotaxis

A micro-transwell chemotaxis assay with mouse pre-B cells L1.2 transfected with the human CCR5 was used to profile CCR5 antagonists. The cells were grown in RPMI1640 with glutamax supplemented with 1% nonessential amino acids, sodium pyruvate, penicillin/streptomycin, 50 µM β-mercaptoethanol (referred herein as complete RPMI) and 10% heat inactivated FCS. The cells were routinely kept in culture at a density of less than $1.5×10^6$ cells/ml. On the day before the experiment, the cells were diluted to a density of $0.2×10^6$ cells/ml. Chemotaxis assays were performed with MultiScreen-MIC 96-well plates with 5-µm pore polycarbonate filters. Cell suspensions and MIP-1α dilutions were made in complete RPMI containing 1% human albumin. 100 µl of $2×10^6$ cells/ml was added into the wells of the filter plate, and then the filter plate was gently placed into the receiver plate containing 150 µl of medium control or a given MIP-1α dilution. For assessing the inhibitory effect of the compounds on CCR5-mediated chemotaxis, cells, MIP-1α and compounds were prepared as 2-fold concentrated solutions, mixed and placed into the filter plate and receiver plate. It is important to note that the compounds were pre-diluted in DMSO at a 2000-fold molar excess so that the final DMSO concentration was 0.05% in the chemotaxis assay. To ensure an uniform concentration, the compounds were added to the upper compartment (cells) as well as to the lower compartment (MIP-1α). After migration for 4 hr at 37° C. in an incubator, the filter plate was carefully removed from the receiver plate and discarded. The migrated cells in the receiver plate were resuspended and transferred into round-bottom 96-well plate, centrifuged and resuspended in 100 µl PBS containing 2% FCS and 0.1% $NaN_3$. The input cells (100 µl) were similarly processed. For the calculation of the specific migration, a fixed number of beads (10000) in 20 µl FACS buffer was added and the suspension was analyzed by flow cytometry using a FACScalibur equipped with an AutoSampler MAS-1 and CellQuest software with established settings for 300-19 cells and beads. Chemotaxis is expressed as percent of input cells using the following formula: ((% cells/% beads)/(% input cells/% input beads))*100.

d) CCR5 Membrane Binding Assay

Human CCR5 is used to generate stable transfectants in CHO K1 cells. Membranes prepared from these CCR5 transfectants are used in a radioligand binding assay using 125-1-MIP-1α as a ligand and the compounds of formula I are tested for inhibitory activity. The data are reported as $IC_{50}$, i.e. the concentration of compound required to achieve 50% inhibition of [I-125]MIP-1α binding. In this assay, compounds of formula I have an $IC_{50}$ between 0.004 and 10 µM.

In these assays, compounds of formula I have an $IC_{50}$ between 0.0002 and 10 µM. Concrete data are provided in the enclosed tables:

| Example | CCR2 IC50 [nM] |
|---|---|
| 1 | 12.0 |
| 6 | 24.3 |
| 7 | 13.8 |
| 8 | 10.8 |

-continued

| Example | CCR2 IC50 [nM] |
|---|---|
| 10 | 1.5 |
| 11 | 2.3 |
| 12 | 0.2 |
| 13 | 2.7 |
| 15 | 0.4 |
| 16 | 0.8 |
| 17 | 0.8 |
| 18 | 0.2 |
| 19 | 0.7 |
| 20 | 0.9 |
| 21 | 1.6 |
| 22 | 7.4 |
| 23 | 12.5 |

| Example | CCR5 IC50 [nM] |
|---|---|
| 1 | 13.2 |
| 3 | 13.8 |
| 6 | 27.0 |
| 7 | 11.9 |
| 8 | 58.5 |
| 10 | 10.6 |
| 12 | 0.5 |
| 15 | 4.8 |
| 13 | 5.8 |
| 16 | 2.9 |
| 18 | 3.3 |
| 20 | 3.2 |
| 21 | 9.0 |
| 23 | 12.1 |

The Agents of the invention are effective as dual CCR-2 and CCR-5 antagonists. Thus the Agents of the invention are useful for the prophylaxis and treatment of CCR-2 and CCR-5 mediated diseases or medical conditions. CCR-2 and CCR-5 play an important role in leukocyte trafficking, in particular in monocyte migration to inflammatory sites and thus the agents of the invention may be used to inhibit monocyte migration e.g. in the treatment of inflammatory conditions, allergies and allergic conditions, autoimmune diseases, chronic pain, graft rejection, cancers which involve leukocyte filtration, stenosis or restenosis, atherosclerosis, rheumatoid arthritis, osteoarthritis and chronic pain.

Diseases or conditions which may be treated with the Agents of the Invention include:
Inflammatory or allergic conditions, including respiratory allergic diseases such as asthma, allergic rhinitis, COPD, hypersensitivity lung diseases, hypersensitivity pneumonitis, interstitial lung disease (ILD), (e.g. idiopathic pulmonary fibrosis, or ILD associated with autoimmune diseases such as RA, SLE, etc.); chronic obstructive pulmonary disease, anaphylaxis or hypersensitivity responses, drug allergies (e.g. to penicillins or cephalosporins), and insect sting allergies; inflammatory bowel diseases, such as Crohn's disease and ulcerative colitis; spondyloarthropathies, sclerodoma; psoriasis and inflammatory dermatoses such as dermatitis, eczema, atopic dermatitis, allergic contact dermatitis, urticaria; vasculitis;
Autoimmune diseases, in particular autoimmune diseases with an aetiology including an inflammatory component such as arthritis (for example rheumatoid arthritis, arthritis chronica progrediente, psoriatic arthritis and arthritis deformans) and rheumatic diseases, including inflammatory conditions and rheumatic diseases involving bone loss, inflammatory pain, hypersensitivity (including both airways hypersensitivity and dermal hypersensitivity) and allergies. Specific auto-immune diseases for which Antibodies of the Invention may be employed include autoimmune haematological disorders (including e.g. hemolytic anaemia, aplastic anaemia, pure red cell anaemia and idiopathic thrombocytopenia), systemic lupus erythematosus, polychondritis, sclerodoma, Wegener granulomatosis, dermatomyositis, chronic active hepatitis, myasthenia gravis, psoriasis, Steven-Johnson syndrome, idiopathic sprue, autoimmune inflammatory bowel disease (including e.g. ulcerative colitis, Crohn's disease and Irritable Bowel Syndrome), autoimmune thyroiditis, Behcet's disease, endocrine opthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, and glomerulonephritis (with and without nephrotic syndrome, e.g. including idiopathic nephrotic syndrome or minimal change nephropathy);
graft rejection (e.g. in transplantation including heart, lung, combined heart-lung, liver, kidney, pancreatic, skin, or corneal transplants) including allograft rejection or xenograft rejection or graft-versus-host disease, and organ transplant associated arteriosclerosis; atherosclerosis;
cancer with leukocyte infiltration of the skin or organs; breast cancer;
stenosis or restenosis of the vasculature, particularly of the arteries, e.g. the coronary artery, including stenosis or restenosis which results from vascular intervention, as well as neointimal hyperplasia;
stroke;
and other diseases or conditions involving inflammatory responses including reperfusion injury, hematologic malignancies, cytokine induced toxicity (e.g. septic shock or endotoxic shock), polymyositis, dermatomyositis, and granulomatous diseases including sarcoidosis; infectious diseases, including HIV and AIDS.

The term "treatment" as used herein is to be understood as including both therapeutic and prophylactic modes of therapy e.g. in relation to the treatment of neoplasia, therapy to prevent the onset of clinically or preclinically evident neoplasia, or for the prevention of initiation of malignant cells or to arrest or reverse the progression of premalignant to malignant cells, as well as the prevention or inhibition of neoplasia growth or metastasis. In this context, the present invention is, in particular, to be understood as embracing the use of compounds of the present invention to inhibit or prevent development of skin cancer, e.g. squamus or basal cell carcinoma consequential to UV light exposure, e.g. resultant from chronic exposure to the sun.

Agents of the Invention are particularly useful for treating diseases of bone and cartilage metabolism including osteoarthritis, osteoporosis and other inflammatory arthritides, e.g. rheumatoid arthritis, and bone loss in general, including age-related bone loss, and in particular periodontal disease.

The Agents of the Invention may also be used in ocular applications which include the treatment of ocular disorders, in particular of ocular inflammatory disorders, of ocular pain including pain associated with ocular surgery such as PRK or cataract surgery, of ocular allergy, of photophobia of various etiology, of elevated intraocular pressure (in glaucoma) by inhibiting the production of trabecular meshwork inducible glucocorticoid response (TIGR) protein, and of dry eye disease.

For the above indications, the appropriate dosage will, of course, vary depending upon, for example, the particular Agent of the Invention to be employed, the subject to be treated, the mode of administration and the nature and severity of the condition being treated. However, in prophylactic use, satisfactory results are generally indicated to be obtained at dosages from about 0.05 mg to about 10 mg per kilogram body weight, more usually from about 0.1 mg to about 5 mg per kilogram body weight. The frequency of dosing for prophylactic use will normally be in the range from about once per week up to about once every 3 months, more usually in the range from about once every 2 weeks up to about once every 10 weeks, e.g. once every 4 or 8 weeks. Agent of the Invention is conveniently administered parenterally, intravenously, e.g. into the antecubital or other peripheral vein, intramuscularly, or subcutaneously. For example, a prophylactic treatment typically comprises administering the Agent of the Invention once per month to once every 2 to 3 months, or less frequently.

The Agents of the invention may be administered in combination with another active agent. Suitable active agents include antimetabolites (e.g. methotrexate), anti-TNF agents (e.g. Remicade® (infliximab), Enbrel® (Etanercept), Humira® (adalumimab)), anti-IL-1 agents (e.g. pralnacasan, ACZ885), nucleoside and non-nucleoside reverse transcriptase inhibitors, HIV protease inhibitors, fusion inhibitors and other antiretroviral agents. The active agent or agents may be administered simultaneously, separately or sequentially with the Agent of the invention.

Pharmaceutical compositions of the invention may be manufactured in conventional manner. A composition according to the invention is preferably provided in lyophilized form. For immediate administration it is dissolved in a suitable aqueous carrier, for example sterile water for injection or sterile buffered physiological saline. If it is considered desirable to make up a solution of larger volume for administration by infusion rather as a bolus injection, it is advantageous to incorporate human serum albumin or the patient's own heparinised blood into the saline at the time of formulation. The presence of an excess of such physiologically inert protein prevents loss of antibody by adsorption onto the walls of the container and tubing used with the infusion solution. If albumin is used, a suitable concentration is from 0.5 to 4.5% by weight of the saline solution.

The Agents of the Invention may be administered by any conventional route, e.g. orally, for example in the form of solutions for drinking, tablets or capsules or parenterally, for example in the form of injectable solutions or suspensions. Normally for systemic administration oral dosage forms are preferred, although for some indications the Agents of the Invention may also be administered topically or dermally, e.g. in the form of a dermal cream or gel or like preparation or, for the purposes of application to the eye, in the form of an ocular cream, gel or eye-drop preparation; or may be administered by inhalation, e.g., for treating asthma. Suitable unit dosage forms for oral administration comprise e.g. from 25 to 250 mg of Agent of the Invention per unit dosage.

The Agents of the Invention typically have a favourable pharmacokinetic profile, i.e. such as a relatively fast elimination over time. A faster elimination is typically indicative for an improved tolerability or is typically associable with less side effects. Such may be assessed by determining for example the receptor occupancy of the CCR2 receptor over time.

Receptor occupancy assaying may be performed in 96-well plates. 45 microliters of freshly obtained blood samples are incubated with 5 microliter of a MCP-1 solution (several concentrations for assessing a biding curve). The concentration of said MCP-1 solution is from 0.01 to 100 nanomolar, whereby the dilutions are made in RPMI1640 with glutamax supplemented with 1% nonessential amino acids, sodium pyruvate, penicillin/streptomycin, 50 microliter beta-mercaptoethanol and 1% human albumin.

Said incubation is carried out for 30 min at 37° C., and is then stopped by adding 180 microliter BD FACS lysis solution followed by centrifugation. Said lysis addition and centrifugation is repeated once and the remaining cells are then washed with ice cold FACS buffer (FBS containing 2% FCS and 0.1% $NaN_3$). Thereupon, the cells are stained with antibodies for FACS analysis.

The cells are now triple stained with FITC-conjugated anti-CD14, PE-conjugated anti-HLA-DR and APC-conjugated anti-CCR2. The antibodies are diluted into FACS buffer, supplemented with 3 mg/ml juman IgG, and the staining is performed in a total of 25 microliter for 30 min. on ice. The stained cells are washed twice with cold FACS buffer and then analyzed by flow cytometry using a FACScalibur and CellQuest software. The expression of CCR2 on CD-14- and HLA-DR-positive monocytes is determined and expressed as mean fluorescence intensity (MFI). The relative CCR2 expression is expressed as percent of control staining.

For the compounds of the present invention the enclosed data show a significant reduced receptor blockade after 24 hours when compared to the state-of-the art compounds.

| Example No | Dose (mg/kg) | Receptor blockade After 2 hrs in % | Receptor blockade After 24 hrs in % |
|---|---|---|---|
| WO05/077932 (example 42) | 10 | 100 | 97.2 |
| WO05/077932 (example 86) | 10 | 93.2 | 92.9 |
| WO05/077932 (example 98) | 10 | 92.5 | 88.3 |
| Present invention (example 15) | 10 | 103.2 | 42.6 |
| Present invention (example 16) | 10 | 78.1 | 21.6 |
| Present invention (example 18) | 10 | 88.2 | 43.5 |

The invention claimed is:

1. A compound of formula (I), or a pharmaceutically acceptable salt thereof:

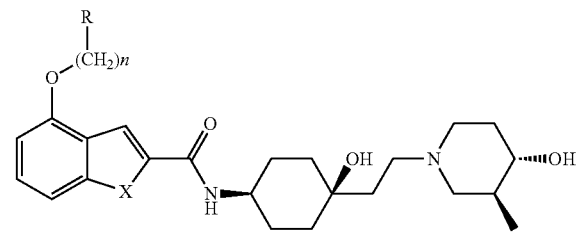

(I)

Wherein:
X is NH;
n is 1 or 2;
R is selected from C3-C18 cycloalkyl, C3-C18 heterocycloalkyl, C5-C18 heteroaryl, or C6-C18 aryl;
R has optionally fused to it a group selected from C3-C8 cycloalkyl, C3-C8 heterocycloalkyl, C6-C8 aryl or C5-C8 heteroaryl;
and R and B are each independently unsubstituted or substituted by R1 which defines one or more groups independently selected from halo, C1-C7 alkoxy, oxo, C1-C7 alkyl, C1-C7 alkoxy-C1-C7 alkoxy, C2-C7 alkenyl, C2-C7 alkenyloxy, amino, aminocarbonyl, carbamoyl, mono- or di-C1-C7 alkylamino, hydroxyl, cyano, mercapto, $C_1$-$C_7$ alkoxycarbonyl, aryl, heteroaryl, carboxy, sulfanyl, and sulfonyl; R1 being itself unsubstituted or substituted by one or more groups selected from halo, hydroxyl, cyano, C1-C6 alkyl, C1-C6 alkoxy, C2-C7 alkenyl, C2-C7 alkenyloxy, amino, aminocarbonyl, carbamoyl, mono- or di-C1-C7 alkylamino, hydroxyl, cyano, mercapto, $C_1$-$C_7$ alkoxycarbonyl, aryl, heteroaryl, and carboxy.

2. The compound according to claim 1 wherein R is C5-C18 heteroaryl and R and B are each independently unsubstituted or substituted by R1 as defined in claim 1, or a pharmaceutically acceptable salt thereof.

3. The compound according to claim 1 wherein R is benzofuranyl, or a pharmaceutically acceptable salt thereof.

4. The compound according to claim 1 selected from:
- 4-Cyclobutylmethoxy-1H-indole-2-carboxylic acid {4-hydroxy-4-[2-((3S,4S)-4-hydroxy-3-methyl-piperidin-1-yl)-ethyl]-cyclohexyl}-amide;
- 4-(Tetrahydro-furan-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide;
- 4-(Furan-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide;
- 4-(2-Chloro-thiazol-4-ylmethoxy)-1H-indole-2-carboxylic acid {4-hydroxy-4-[2-((3S,4S)-4-hydroxy-3-methyl-piperidin-1-yl)-ethyl]-cyclohexyl}-amide;
- 4-(6-Methoxy-pyridin-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide;
- 4-(4-Oxo-4,5,6,7-tetrahydro-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide;
- 4-(6,6-Dimethyl-4-oxo-4,5,6,7-tetrahydro-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide;
- 4-[(S)-1-(2,3-Dihydro-benzofuran-3-yl)methoxy]-1H-indole-2-carboxylic acid {4-hydroxy-4-[2-((3S,4S)-4-hydroxy-3-methyl-piperidin-1-yl)-ethyl]-cyclohexyl}-amide;
- 4-((R,S)-6-Methoxy-2,3-dihydro-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide;
- 4-(4-Methoxy-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide;
- 4-(4,6-Difluoro-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide;
- 4-(5-Chloro-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide;
- 4-(6-Methoxy-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide;
- 4-(6-Ethoxy-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide;
- 4-(6-Cyclopropylmethoxy-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide;
- 4-[6-(2-Ethoxy-ethoxy)-benzofuran-3-ylmethoxy]-1H-indole-2-carboxylic acid {4-hydroxy-4-[2-((3S,4S)-4-hydroxy-3-methyl-piperidin-1-yl)-ethyl]-cyclohexyl}-amide;
- 4-[6-((RS)-2-Methoxy-1-methyl-ethoxy)-benzofuran-3-ylmethoxy]-1H-indole-2-carboxylic acid {4-hydroxy-4-[2-((3S,4S)-4-hydroxy-3-methyl-piperidin-1-yl)-ethyl]-cyclohexyl}-amide;
- 4-[6-(2-Isopropoxy-ethoxy)-benzofuran-3-ylmethoxy]-1H-indole-2-carboxylic acid {4-hydroxy-4-[2-((3S,4S)-4-hydroxy-3-methyl-piperidin-1-yl)-ethyl]-cyclohexyl}-amide;
- 4-[6-(3-Methoxy-propoxy)-benzofuran-3-ylmethoxy]-1H-indole-2-carboxylic acid {4-hydroxy-4-[2-((3S,4S)-4-hydroxy-3-methyl-piperidin-1-yl)-ethyl]-cyclohexyl}-amide;
- 4-[6-(3-Ethoxy-propoxy)-benzofuran-3-ylmethoxy]-1H-indole-2-carboxylic acid {4-hydroxy-4-[2-((3S,4S)-4-hydroxy-3-methyl-piperidin-1-yl)-ethyl]-cyclohexyl}-amide;
- 4-{6-[(S)-(Tetrahydro-furan-3-yl)oxy]-benzofuran-3-ylmethoxy}-1H-indole-2-carboxylic acid {4-hydroxy-4-[2-((3S,4S)-4-hydroxy-3-methyl-piperidin-1-yl)-ethyl]-cyclohexyl}-amideamide;
- 4-(6-Fluoro-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide; or
- 4-(7-Methoxy-benzofuran-3-ylmethoxy)-1H-indole-2-carboxylic acid {4-hydroxy-4-[2-((3S,4S)-4-hydroxy-3-methyl-piperidin-1-yl)-ethyl]-cyclohexyl}-amide;
- 4-[2-(2-Methoxy-phenyl)-ethoxy]-1H-indole-2-carboxylic acid {4-hydroxy-4-[2-((3S,4S)-4-hydroxy-3-methyl-piperidin-1-yl)-ethyl]-cyclohexyl}-amide;
- 4-[2-(3-Methoxy-phenyl)-ethoxy]-1H-indole-2-carboxylic acid {4-hydroxy-4-[2-((3S,4S)-4-hydroxy-3-methyl-piperidin-1-yl)-ethyl]-cyclohexyl}-amide;
- 4-[2-(4-Methoxy-phenyl)-ethoxy]-1H-indole-2-carboxylic acid {4-hydroxy-4-[2-((3S,4S)-4-hydroxy-3-methyl-piperidin-1-yl)-ethyl]-cyclohexyl}-amide;
- 4-[2-(2-Methoxy-pyridin-3-yl)-ethoxy]-1H-indole-2-carboxylic acid {4-hydroxy-4-[2-((3S,4S)-4-hydroxy-3-methyl-piperidin-1-yl)-ethyl]-cyclohexyl}-amide;
- 4-[2-(6-Methoxy-pyridin-3-yl)-ethoxy]-1H-indole-2-carboxylic acid {4-hydroxy-4-[2-((3S,4S)-4-hydroxy-3-methyl-piperidin-1-yl)-ethyl]-cyclohexyl}-amide; or
- 4-[2-(6-Methoxy-benzofuran-3-yl)-ethoxy]-1H-indole-2-carboxylic acid {4-hydroxy-4-[2-((3S,4S)-4-hydroxy-3-methyl-piperidin-1-yl)-ethyl]cyclohexyl}-amide, or a pharmaceutically acceptable salt thereof.

5. A pharmaceutical composition comprising a compound according to claim 1, or a pharmaceutically acceptable salt thereof, and a pharmaceutically acceptable diluent or carrier.

6. A process for the preparation of a compound of formula (I) as defined in claim 1 comprising reacting a compound of formula (III):

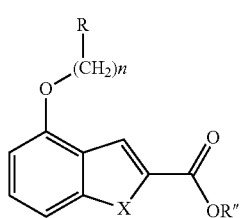 (III)
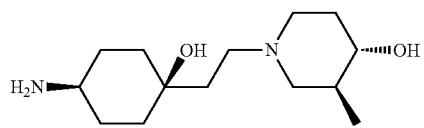 (IV)
wherein R" is H or a $C_1$-$C_7$ alkyl group, with a compound of formula (IV)
and recovering the resultant compound of formula (I) in free or salt form.
7. A compound obtainable by the process of claim 6.
* * * * *

UNITED STATES PATENT AND TRADEMARK OFFICE
CERTIFICATE OF CORRECTION

PATENT NO. : 8,354,431 B2
APPLICATION NO. : 12/527469
DATED : January 15, 2013
INVENTOR(S) : Hersperger et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 396 days.

Signed and Sealed this
Second Day of April, 2013

Teresa Stanek Rea
*Acting Director of the United States Patent and Trademark Office*